US005506131A

United States Patent [19]

Harris et al.

[11] Patent Number: 5,506,131

[45] Date of Patent: * Apr. 9, 1996

[54] IMMORTALIZED HUMAN CELL LINES CONTAINING EXOGENOUS CYTOCHROME P450 GENES

[75] Inventors: Curtis C. Harris, Bethesda; Harry V. Gelboin, Chevy Chase; Frank J. Gonzalez, Bethesda, all of Md.; Katharine C. Macé, Lousanne; Andrea M. A. Pfeifer, Vevey, both of Switzerland

[73] Assignee: The United States of America as represented by the Department of Health and Human Services, Washington, D.C.

[*] Notice: The portion of the term of this patent subsequent to Oct. 18, 2011, has been disclaimed.

[21] Appl. No.: 65,201

[22] Filed: May 19, 1993

Related U.S. Application Data

[63] Continuation-in-part of Ser. No. 869,818, Apr. 13, 1992, Pat. No. 5,356,806, which is a continuation-in-part of Ser. No. 787,777, Nov. 6, 1991, Pat. No. 5,164,313, which is a continuation-in-part of Ser. No. 58,387, Jun. 5, 1987, abandoned, said Ser. No. 869,818, is a continuation-in-part of Ser. No. 636,712, Jan. 2, 1991, Pat. No. 5,443,954, which is a continuation-in-part of Ser. No. 265,883, Nov. 1, 1988, abandoned, which is a continuation-in-part of Ser. No. 114,508, Oct. 30, 1987, Pat. No. 4,885,238.

[51] Int. Cl.$^6$ .................................................. C12N 5/10
[52] U.S. Cl. ................................. 435/240.2; 435/6
[58] Field of Search ........................... 435/6, 7.21, 69.1, 435/172.2, 172.3, 240.2; 935/70

[56] References Cited

U.S. PATENT DOCUMENTS

| | | | |
|---|---|---|---|
| 4,675,002 | 6/1987 | Viles et al. | 604/5 |
| 4,816,395 | 3/1989 | Hancock | 435/29 |
| 4,885,238 | 12/1989 | Reddel | 435/29 |
| 5,164,313 | 11/1992 | Gelboin | 435/189 |
| 5,356,806 | 10/1994 | Harris et al. | 435/240.2 |

FOREIGN PATENT DOCUMENTS

| | | | |
|---|---|---|---|
| WO89/03994 | 5/1989 | WIPO . | |
| WO92/07085 | 4/1992 | WIPO | C12Q 1/100 |

OTHER PUBLICATIONS

Nebert et al., *DNA and Cell Biol.*, vol. 10, 1991, pp. 1–14.
Bayad et al., *Biochem. Pharmacol.*, vol. 42, 1991, pp. 1345–1351.
Harris et al., *Cancer Research*, vol. 47, 1987, pp. 1–10.
U.S. Ser. No. 07/377,967, filed Dec. 19, 1989 by Cole et al.
Lechner et al., "Non-tumorigenic human liver epithelial cell cultures for chemical and biological carcinogenesis investigations," *J. Cell. Biochemistry* Supp. 15D, p. 140 (1991).
Crespi et al., "Stable expression of human cytochrome P450IA2 cDNA in a human lymphoblastoid cell line: role of the enzyme in the metabolic activation of aflatoxin $B_1$," *Molecular Carcinogenesis*, 3(1):5–8 (1990).
Crespi et al., "A metabolically competent human cell line expressing five cDNAs encoding procarcinogen-activating enzymes: application to mutagenicity testing," *Chem. Res. Toxicol.*, 4(5):566–572 (Oct. 1991).
Macé et al., "Increased activation of promutagens in a human bronchial epithelial cell line stably expressing the human cytochrome P450 IA2," Proceedings of the 83rd Annual Meeting of the American Association for Cancer Research, Abstract No. 945; vol. 33, Mar. 1992, May 20–23, 1992, San Diego, CA.
Arthur I. Grayzel, et al., "The Effects of Inhibitors Of Protein Synthesis On The Synthesis of Heme In Rabbit Reticulocytes," *Biochemical and Biophysical Research Communications*, 28(5) (1967).
R. C. Garner and A. E. M. McLean, "Separation of HAEM Incorporation From Protein Synthesis In Liver Microsomes," *Biochemical and Biophysical Research Communications*, 37(6):883–887 (1969).
K. W. Bock and P. Siekevitz, "Turnover Of HEME And Protein Moieties Of Rat Liver Microsomal Cytochrome $b_5$," *Biochemical and Biophysical Research Communications*, 41(2):374–380 (1970).
Manford K. Patterson, Jr., "Measurement of Growth and Viability of Cells in Culture," *Methods in Enzymology*, 58:141–152 (1979).
Harry V. Gelboin, "Benzo[α]pyrene Metabolism, Activation, and Carcinogenesis: Role and Regulation of Mixed--Function Oxidases and Related Enzymes," *Physiological Reviews*, 60(4):1107–1166 (1980).
Gwen S. Duthu, et al., "Characterization of NADPH–cytochrome *P–450* reductase in a mouse hepatoma cell line," *Biol. Abstr.*, 76(10):#73560 (1983).
John F. Lechner, et al., "Differential Control by Platelet Factors of Squamous Differentiation in Normal and Malignant Human Bronchial Epithelial Cells," *Cancer Research*, 43:5915–5921 (1983).
Shioko Kimura, et al., "The Murine *Ah* Locus," *The Journal of Biological Chemistry*, 259(17):10705–10713 (1984).
Sekhar Chakrabarti, et al., "Vaccinia Virus Expression Vector: Coexpression of β–Galactosidase Provides Visual Screening of Recombinant Virus Plaques," *Molecular and Cellular Biology*, 5(12):3403–3409 (1985).
Pietro Ghezzi, et al., "Role of reactive oxygen intermediates in the interferon–mediated depression of hepatic drug metabolism and protective effect of N–acetylcysteine in mice," *Biological Abstracts*, 80(12):AB–961:#91194 (1985).

(List continued on next page.)

Primary Examiner—Mindy Fleisher
Assistant Examiner—James Ketter
Attorney, Agent, or Firm—Townsend and Townsend and Crew

[57] ABSTRACT

Non-tumorigenic, stable, human bronchial and liver epithelial cell lines are provided wherein the cell lines are capable of expressing human cytochrome P450 genes which have been inserted into the cell lines. Also provided are methods and kits for identifying potential mutagens, cytotoxins, carcinogens, chemotherapeutic and chemo-preventive agents utilizing these cell lines.

11 Claims, 12 Drawing Sheets

OTHER PUBLICATIONS

John F. Lechner and Moira A. LaVeck, "A Serum–Free Method For Culturing Normal Human Bronchial Epithelial Cells At Clonal Density," *Journal of Tissue Culture Methods,* 9(2):43–48 (1985).

Kenji Oeda, et al., "Expression of Rat Liver Cytochrome P–450MC cDNA in *Saccharomyces cerevisiae,*" *DNA,* 4(3):203–210 (1985).

Hiroyuki Sadano and Tsuneo Omura, "Incorporation of Heme to Microsomal Cytochrome P–450 in the Absence of Protein Biosynthesis," *J. Biochem.,* 98(5):1321–1331 (1985).

William T. Wickner and Harvey F. Lodish, "Multiple Mechanisms of Protein Insertion Into and Across Membranes," *Science,* 230:400–406 (1985).

George H. Yoakum, et al., "Transformation of Human Bronchial Epithelial Cells Transfected by Harvey *ras* Oncogene," *Science,* 227:1174–1178 (1985).

Philippe H. Beaune, et al., "Isolation and sequence determination of a cDNA clone related to human cytochrome P–450 nifedipine oxidase," *Proc. Natl. Acad. Sci. USA,* 83:8064–8068 (1986).

Anil K. Jaiswal, et al., "Human $P_3$450: cDNA and complete amino acid sequence," *Nucleic Acids Research,* 14(16):6773–6774 (1986).

Y. Ke, et al., "Human Bronchial Epithelial Cells Transformed by SV40 Gene(s) Retain the Ability to Undergo Terminal Squamous Differentiation," *J. Cell Biol.,* 103(2): 27a:#95 (1986).

M. Mackett and G. L. Smith, "Vaccinia Virus Expression Vectors," *J. gen. Virol.,* 67:2067–2082 (1986).

Tohru Masui, et al., "Growth and Differentiation of Normal and Transformed Human Bronchial Epithelial Cells," *Journal of Cellular Physiology Supplement,* 4:73–81 (1986).

Toshitaro Nakagawa, et al., "Sodium N–Butyrate Modulates The Transcription And Posttranscriptional Processing of the Calcitonin Gene in Human Medullary Thyroid Carcinoma," *Federation Proceedings,* 46:718:#2352 (1987).

R. R. Reddel, et al., "Human Mesothelial Cells Are Transformed By Transfection With SV40 Large T Antigen Gene," *J. Cell Biol.,* 103(2): 27a:#94 (1986).

Byung–Joon Song, et al., "Complementary DNA and Protein Sequences of Ethanol–inducible Rat and Human Cytochrome P–450s," *The Journal of Biological Chemistry,* 261(35):16689–16697 (1986).

Edward B. Stephens, et al., "Surface expression of viral glycoproteins in polarized in epithelial cells infected with recombinant vaccinia viral vectors," *Biol. Abstr.,* 81(12):AB–560:#112680 (1986).

Mauricio X. Zuber, et al., "Expression of Bovine 17α–Hydroxylase Cytochrome P–450 cDNA in Nonsteroidogenic (COS 1) Cells," *Science,* 234:1259–1261 (1986).

Narayana Battula, et al., "Expression of $P_1$–450 and $P_3$–450 DNA coding sequences as enzymatically active cytochromes P–450 in mammalian cells," *Proc. Natl. Acad. Sci. USA,* 84:4073–4077 (1987).

Douglas E. Brash et al., "Strontium Phosphate Transfection of Human Cells in Primary Culture: Stable Expression of the Simian Virus 40 Large–T–Antigen Gene in Primary Human Bronchial Epithelial Cells," *Molecular and Cellular Biology,* 7(5):2031–2034 (1987).

B. I. Gerwin, et al., "Growth Factor Production By Normal Human Mesothelial Cells and Mesothelioma Cell Lines," *European Association for Cancer,* p. 1752 (1987).

Brenda Gerwin, et al., "Response To Growth Factors By Normal Human Mesothelial Cells And Their Autocrine Production By Human Mesothelioma Cell Lines," *J. Cell. Biochem.,* Supplement 11, Abstract A217, p. 58 (1987).

Shioko Kimura, et al., "cDNA and amino acid sequences of two members of the human P450IIC gene subfamily," *Nucleic Acids Research,* 15(23):10053–10054 (1987).

J. F. Lechner, et al., "Normal Human Mesothelial Cells Are Responsive To Unusual Combinations Of Growth Factors," *Proceedings of AACR,* 28:60:#240 (1987).

R. Reddel, et al., "Development of Non–Tumorigenic Human Mesothelial Cell Lines With Transfected SV40 Large T Antigen Gene," *European Association for Cancer,* p. 1794 (1987).

R. R. Reddel, et al., "Establishment of Non–Tumorigenic Human Bronchial Epithelial Cell Lines," *Proc. Amer. Assoc. Cancer Res.,* 28:118:#469 (1987).

J. S. Rhim, et al., "An In Vitro Multi–Step Model for Human Epithelial Cell Carcinogenesis," *Proc. Amer. Assoc. Cancer Res.,* 28:120:#475 (1987).

Sasajima, et al., "Effects of tumor promoters and cocarcinogens on growth and differentiation of cultured human esophageal epithelial cells," *J. National Cancer Institute,* 78(3):419–423 (1987).

Diane R. Umbenhauer, et al., "Cloning and Sequence Determination of a Complementary DNA Related to Human Liver Microsomal Cytochrome P–450 S–Mephenytoin 4–Hydroxylase," *Biochemistry,* 26:1094–1099 (1987).

Paul Amstad, et al,. "Neoplastic Transformation of a Human Bronchial Epithelial Cell Line by a Recombinant Retrovirus Encoding Viral Harvey *ras,*" *Molecular Carcinogenesis,* 1:151–160 (1988).

Johannes Doehmer, et al., "Stable expression of rat cytochrome P–450IIb1 cDNA in Chinese hamster cells (V79) and metabolic activation of aflatoxin $B_1$," *Proc. Natl. Acad. Sci. USA,* 85:5769–5773 (1988).

Frank J. Gonzalez, et al., "Human Debrisoquine 4–Hydroxylase (P450IID1): cDNA and Deduced Amino Acid Sequence and Assignment of the *CYP2D* Locus to Chromosome 22," *Genomics,* 2:174–179 (1988).

Frank J. Gonzalez, et al., "Human P450PCN1: Sequence, Chromosome Localization, and Direct Evidence through cDNA Expression That P450PCN1 Is Nifedipine Oxidase," *DNA,* 7(2):79–86 (1988).

Roger R. Reddel, et al., "Human Bronchial Epithelial Cells Neoplastically Transformed by v–Ki–*ras:* Altered response to Inducers of Terminal Squamous Differentiation," *Oncogene Research,* 3:401–408 (1988).

Roger R. Reddel, et al., "Transformation of Human Bronchial Epithelial Cells by Infection with SV40 or Adenovirus–12 SV40 Hybrid Virus, or Transfection via Stronitum Phosphate Coprecipitation with a Plasmid Containing SV40 Early Region Genes," *Cancer Research,* 48:1904–1909 (1988).

Morio Umeno, et al., "Human Ethanol–Inducible P450IIE1: Complete Gene Sequence, Promoter Characterization, Chromosome Mapping, and cDNA–Directed Expression," *Biochemistry,* 27:9006–9013 (1988).

R. Daniel Bonfil, et al., "Invasive and Metastatic Potential of a v–Ha–ras–Transformed Human Bronchial Epithelial Cell Line," *Journal of the National Cancer Institute,* 81(8):587–594 (1989).

C. L. Crespi, et al., "Transfection of a human cytochrome P–450 gene into the human lymphoblastoid cell line, AHH-1, and use of the recombinant cell line in gene mutation assays," *Carcinogenesis*, 10(2):295–301 (1989).

Robin L. Davies, et al., "Development of a human cell line by selection and drug–metabolizing gene transfection with increased capacity to activate promutagens," *Carcinogenesis*, 10(5):885–891 (1989).

Andrea M. A. Pfeifer, et al., "Control of Growth and Squamous Differentiation in Normal Human Bronchial Epithelial Cells by Chemical and Biological Modifiers and Transferred Genes," *Environmental Health Perspectives*, 80:209–220 (1989).

A. M. A. Pfeifer, et al., "Cooperation of c–*raf*–1 and c–*myc* protooncogenes in the neoplastic transformation of simian virus 40 large tumor antigen–immortalized human bronchial epithelial cells," *Proc. Natl. Acad. Sci. USA*, 86:10075–10079 (1989).Roger R. Reddel, et al., "Tumorigenicity of Human Mesothelial Cell Line Transfected With EJ–ras Oncogene," *Journal of the National Cancer Institute*, 81(12):945–948 (1989).

Hitoshi Ura, et al, "Expression of Type IV Collagenase and Procollagen Genes and Its Correlation with the Tumorigenic, Invasive, and Metastatic Abilities of Oncogene–transformed Human Bronchial Epithelial Cells," *Cancer Research*, 49:4615– 4621 (1989).

C. L. Crespi, et al., "The Development of a Panel of Human Cell Lines Expressing Specific Human Cytochrome P450 cDNAs," *Progress in Clinical and Biological Research*, 340B:97–106, Mendelsohn and Albertini (eds), Wiley–Liss: New York, (1990).

Charles L. Crespi, et al., "Human cytochrome P450IIA3: cDNA sequence, role of the enzyme in the metabolic activation of promutagens, comparison to nitrosamine activation by human cytochrome P450IIE1," *Carcinogenesis*, 11(8):1293–1300 (1990).

Brenda I. Gerwin, et al., "TGF–$\beta_1$ modulation of urokinase and PAI–1 expression in human bronchial epithelial cells," *Am. J. Physiol.*, 259:L262–269 (1990).

Bernard Moss, "Poxviridae and their replication," *Virology*, 2nd ed., B. N. Fields (ed.), Raven Press, Ltd.: New York, pp. 2079–2111 (1990).

Shigeru Yamano, et al., "The *CYP2A3* Gene Product Catalyzes Coumarin 7–Hydroxylation in Human Liver Microsomes," *Biochemistry*, 29:1322–1329 (1990).

Narayana Battula, et al., "Cytochrome P4501A2 Constitutively Expressed From Transduced DNA Mediates Metabolic Activation and DNA–Adduct Formation of Aromatic Amine Carcinogens in NIH 3T3 Cells," *Molecular Carcinogenesis*, 4:407–414 (1991).

Ronald W. Estabrook, et al., "The Heterologous Expression Of The Cytochromes P450: A New Approach For The Study Of Enzyme Activities And Regulation," *Adv. Enzyme Regul.*, 31:365–383 (1991).

Monica Hollstein, et al., "p53 Mutations in Human Cancers," *Science*, 253:49–53 (1991).

Teresa A. Lehman, et al., "Oncogenes and Tumor–Suppressor Genes," *Environmental Health Perspectives*, 93:133–144 (1991).

A. M. A. Pfeifer, et al., "Human Bronchial Epithelial Cells Transformed by the c–*raf*–1 and c–*myc* Protooncogenes Induce Multidifferentiated Carcinomas in Nude Mice: A Model for Lung Carcinogenesis," *Cancer Research*, 51:3793–3801 (1991).

Baker et al., "Suppression of human colorectal carcinoma cell growth by wild–type p53," *Science*, 249:912–915 (1990).

Pfeifer et al., "Simian virus 40 large tumor antigen–immortalized normal human liver epithelial cells express hepatocyte characteristics and metabolize chemical carcinogens," *Proc. Natl. Acad. Sci.* (*USA*), 90:5123–5127 (Jun. 1993).

Macé et al., "High expression of cytochrome P–450 1A2 in SV40 T–antigen immortalized adult liver epithelial cell lines," *Proc. Amer. Assoc. Cancer Res.*, 34:174 (Mar. 1993).

IMMORTALIZED HUMAN CELL LINES CONTAINING EXOGENOUS CYTOCHROME P450 GENES

CROSS-REFERENCE TO RELATED APPLICATIONS

This application is a continuation-in-part of Ser. No. 07/869,818 filed on Apr. 13, 1992, now U.S. Pat. No. 5,356,806, which is a continuation-in-part application of Ser. No. 07/787,777, filed on Nov. 6, 1991, now U.S. Pat. No. 5,164,313, which was a continuation-in-part application of Ser. No. 07/058,387, filed on Jun. 5, 1987, now abandoned. Ser. No. 07/869,818, now U.S. Pat. No. 5,356,806, also is a continuation-in-part application of Ser. No. 07/636,712, filed on Jan. 2, 1991, now U.S. Pat. No. 5,443,954, which was a continuation-in-part application of Ser. No. 07/265,883, filed on Nov. 1, 1988, now abandoned, which was a continuation-in-part application of Ser. No. 07/114,508, filed on Oct. 30, 1987, now issued as U.S. Pat. No. 4,885,238.

BACKGROUND OF THE INVENTION

The invention is related to immortalized human bronchial epithelial cells and human liver epithelial cells containing various cytochrome P450 genes and the uses of these cells. The invention is also related to the construction and application of recombinant vectors containing DNA sequences for encoding, and efficient expression-of, enzymatically active cytochromes P450 in mammalian cells.

The cytochromes P450 are a large family of hemoprotein enzymes capable of metabolizing xenobiotics such as drugs, carcinogens and environmental pollutants as well as endobiotics such as steroids, fatty acids and prostaglandins. Some members of the cytochrome P450 family are inducible in both animals and cultured cells, while other constitutive forms are non-inducible. This group of enzymes has both harmful and beneficial activities. The harmful activity is the metabolic conversion of xenobiotics to toxic, mutagenic and carcinogenic forms. The beneficial activity is the detoxification of xenobiotics (Gelboin, *Physiol. Rev.*, 60:1107–1166, 1980).

In animals, multiple molecular forms of cytochrome P450s are expressed simultaneously and they all exhibit common physical and biological properties. The multiplicity and common properties of cytochromes P450 make it difficult to separate their different forms, especially the minor forms. Even in situations where P450 cytochromes have been isolated in purified form by conventional enzyme purification procedures, they have been removed from the natural biological membrane association and therefore require the addition of NADPH-cytochrome P450 reductase and other cell fractions for enzymatic activity. These additional factors have prevented a clearer understanding of the role and function of the individual cytochrome forms in metabolism, detoxification, and activation of both xenobiotic and endobiotic substrates.

Toxicological testing of drugs, potential carcinogens, food products, food additives and food contaminants has been performed in animals and more recently in in vitro systems, such as bacteria (Ames test) and animal cell culture models. These systems are disadvantaged since they do not have human-specific metabolism. Therefore, extrapolation to determine the human risk is difficult and potentially inaccurate. The bacterial test systems and some of the animal cell culture models lack complete metabolic activity and would not detect any harmful compounds which depend upon activation by metabolic pathways, for example, by the cytochrome P450 enzymes. In the past this situation was circumvented by adding metabolizing enzyme isolated from rat livers to the cultured animal cells. This approach poses two significant problems. First, the resulting metabolism is not necessarily the same as in man. Secondly, highly-reactive metabolites might not reach their target molecule and, consequently, escape detection.

Although human metabolizing enzymes have been introduced into a human cell line, this system suffers from serious deficiencies. (Crespi, *Progress in Clinical and Biological Research,* Vol. 340B Mendelsohn and Albertini (eds) Wiley-Liss, New York 97–106, 1990.) The human cells are lymphoblasts which do not constitute a major target tissue of cytotoxins, mutagens, or carcinogens and have no natural cytochrome P450 activity in the absence of inducers. In addition, other enzymes involved in the activation process, for example, epoxide hydrolase, are missing in these cells and must be introduced by gene transfer methodology. This system therefore comprises an artificial model with a questionable correlation to the in vivo situation.

SUMMARY OF THE INVENTION

Therefore, it is desirable to have an in vitro human cell line system which parallels the in vivo human condition. The present invention provides isolated non-tumorigenic human cell lines of bronchial and liver epithelial cell origin with unlimited proliferative potential, resulting in immortalization.

In one embodiment of this invention a non-tumorigenic, stable, human bronchial epithelial cell line is provided wherein the cell line is capable of growing without senescence when cultured in vitro in growth medium and contains an exogenous cytochrome P450 gene which is capable of being expressed in the cell line. The gene can be inserted by transfection or infection. P450 genes expressed in this cell line include 1A1, 1A2, 2A6, 3A3, 3A4, 2B6, 2B7, 2C9, 2D6, and/or 2E1. Preferred cell lines include any one of cell lines BEAS-2B-1A1, BEAS-2B-1A2, BEAS-2B-2A6, BEAS-2B-3A3, BEAS-2B- 3A4, BEAS-2B-2B6, BEAS-2B-2B7, BEAS-2B-2C9, BEAS-2B-2D6, BEAS- 2B-2E1 or a homolog or a derivative of these cell lines. The BEAS-2B-1A1 cell line is a BEAS-2B cell line containing the cytochrome P450 1A1 gene, the BEAS-2B-1A2 cell line is a BEAS- 2B cell line containing the cytochrome P450 1A2 gene, and so forth. P450 genes are preferably operably linked to a cytomegalovirus promoter to obtain efficient expression. A particularly preferred cell line is BEAS-2B-1A2 or a homolog or derivative thereof.

In a second embodiment of this invention a non-tumorigenic, stable, human liver epithelial cell line is provided wherein the cell line is capable of growing without senescence when cultured in vitro in growth medium and contains an exogenous cytochrome P450 gene capable of being expressed in the cell line. The gene can be inserted by transfection or infection. P450 genes expressed in this cell line include 1A1, 1A2, 2A6, 3A3, 3A4, 2B6, 2B7, 2C9, 2D6, and/or 2E1. Preferred cell lines include any one of cell lines THLE-5B-1A1, THLE-5B-1A2, THLE-5B-2A6, THLE-B5-3A3, THLE-5B-3A4, THLE-5B-2B6, THLE-5B-2B7, THLE-5B-2C9, THLE-5B-2D6, THLE-5B-2E1 or a homolog or a derivative of these cell lines. The THLE-5B-1A1 cell line is a THLE-5B cell line containing the cytochrome P450 1A1 gene, the THLE-5B-1A2 cell lines is a THLE-5B cell line containing the cytochrome P450 1A2 gene, and so forth. P450 genes are preferably operably linked to a cytomegalovirus promoter to obtain efficient expression. A particularly preferred cell line is THLE-5B-1A2 or a homolog or derivative thereof.

In another embodiment of this invention, various methods of utilizing the cell lines are described. For example, a method for identifying or testing the mutagenicity, cytotoxicity, or carcinogenicity of an agent is described which comprises the steps of: a) reacting, culturing, or contacting the cell line with an agent suspected of being a mutagen, cytotoxin, or carcinogen, and b) determining or monitoring those effects on, or changes in, the cell line which are indicative of mutagenicity, cytotoxicity, or carcinogenicity.

Also described by this invention is a method for identifying or testing the chemotherapeutic or chemopreventive activity of an agent comprising the steps of: a) reacting, culturing, or contacting the cell line with an agent suspected of being a chemotherapeutic or chemopreventive in the presence of a carcinogen, and b) determining or monitoring those effects on, or changes in, the cell line which are indicative of chemotherapeutic activity. The agent can be added prior to the carcinogen to measure the preventative effects of the agent.

In a further aspect of this invention, a method is provided for determining the metabolites activated by a carcinogen or xenobiotic comprising the steps of: a) reacting, culturing or contacting the cell line with the suspected carcinogen or xenobiotic, and b) identifying the metabolites and/or their effects.

Also provided are diagnostic kits comprising the cell lines, media, and reagents for use in one of the methods.

Various other objects and advantages of the present invention will become apparent from the Detailed Description of the Invention.

BRIEF DESCRIPTION OF THE DRAWINGS

These and other objects, features and many of the attendant advantages of the invention will be better understood upon a reading of the following detailed description when considered in connection with the accompanying drawings wherein.

DESCRIPTION OF THE INVENTION

Figure 1:
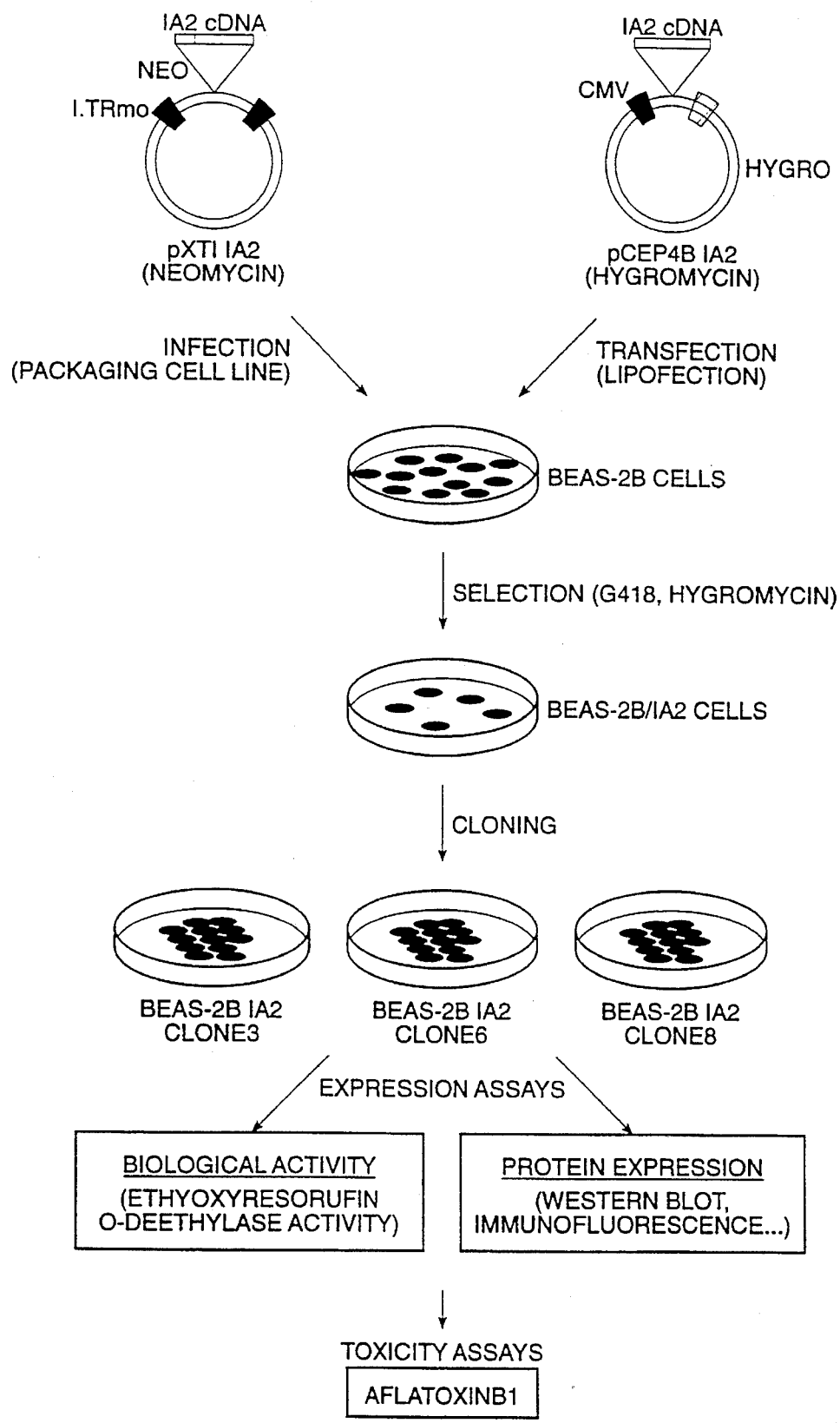
FIG. 1 shows the schematic construction of the recombinant vectors for expressing cytochrome P450 genes and the transfection of the vectors into the BEAS-2B cells.

The above and various other objects and advantages of the present invention are achieved by (a) constructing recombinant vectors containing cDNA sequences encoding cytochrome P450 proteins so that mammalian, especially human, cells when infected or transfected with said recombinant vectors efficiently express the P450 proteins; and (b) providing functionally intact cell lines containing cytochrome proteins without requiring the extraneous addition of NADPH cytochrome P450 reductase for enzymatic activity.

Unless defined otherwise, all technical and scientific terms used herein have the same meaning as commonly understood by one of ordinary skill in the art to which this invention belongs. Although any methods and materials similar or equivalent to those described can be used in the practice or testing of the present invention, the preferred methods and materials are now described. All publications and patent documents referenced in this application are incorporated herein by reference.

I. Immortalized cell lines

The cytochrome-P450-expressing, non-tumorigenic, stable, immortalized cell lines of the invention are derived from lung and liver immortalized cells. Immortalized cells are preferred over primary cells for use as a testing system because of greater reproducibility of results and less onerous preparation for use (once an immortalized cell line has been established). Immortalized cell lines-derived from lung and liver tissues serve as model toxicity systems for the respective tissues from which they were derived. Non-tumorigenic immortalized cells are particularly advantageous because of their greater similarity to normal tissue cells, and because they can be used for determining carcinogenic potential of test substances. The term non-tumorigenic is used to describe cells that do not form tumors when subcutaneously injected into a test animal, such as a mouse. The P450-expressing immortalized cell lines of the present invention are stable in the sense that no detectable reduction of P450 expression occurs after introduction of an exogenous P450 gene for at least 50 passages of the cells.

An immortalized cell line is prepared from cells obtained from a specific tissue of a single human donor. A homolog of that cell line is a second cell line prepared by the same method from the same tissue, but from a different donor. For example, the cell lines THLE-2, THLE-3 and THLE-5 are homologs (see Example 1). Different clonal isolates of a cell line are referred to as derivative cell lines. For example, cell lines THLE-5B-c15.3 and THLE-5B-c15.4 are derivatives of the THLE-5B cell line.

Immortalized cells preferably retain expression of phase II enzymes, such epoxide hydrolase, catalase, glutathione peroxidase, superoxide dismutase and glutathione S-transferase. These enzymes are involved in detoxification of xenobiotics, and their presence increases the authenticity of cellular toxicity testing system as a model for human tissues.

Although immortalized cells lines are preferred over primary cells for use as toxicity testing systems for the reasons discussed above, it has been observed that existing immortalized cell lines do not express, or express at only low levels, one or more P450 cytochromes. The P450 enzymes are required for metabolic processing of certain xenobiotics to toxic, mutagenic or carcinogenic forms. Thus, the immortalized cells of the present invention are transfected with one or more exogenous cytochrome P450 gene to supplement the expression products of endogenous genes. The exogenous P450 gene(s) are operably linked to expression vector(s) such that the gene(s) are capable of being expressed to produce functional P450 enzymes. Functional P450 enzymes are capable of metabolizing one or more of the substrates in Table 1.

II. Cytochrome P450 Genes and Vectors

Genomic or cDNA clones encoding cytochrome P450 genes may be isolated using hybridization probes designed on the basis of the nucleotide or amino acid sequences for the desired gene. The probes can be constructed by chemical synthesis or by polymerase chain reactions using primers based upon sequence data to amplify DNA fragments from pools or libraries. (U.S. Pat. Nos. 4,683,195 and 4,683,202.) al., *Proc. Natl. Acad. Sci. U.S.A.*, 83:8064–8068, 1986 and Gonzales, et al., *DNA*, 7:79–86, 1988). Cytochrome P450 1A2 is described by Jaiswal, et al., *Nucl. Acids Res.*, 14:6773–6774, 1986; 2A3 by Yamano, et al., *Biochem.*, 29:1322–1329, 1990; and 2D6 by Gonzalez, et al., *Genomics*, 2:174–179, 1988.

The members of the cytochrome P450 family differ from each other in substrate specificity and in the tissue types in which they are characteristically expressed. Table 1 shows the tissues in which the various p450 cytochromes are characteristically expressed and also lists suitable carcinogenic substrates for testing for the expression of a particular P450 cytochrome in a cell line. The various members of the cytochrome P450 family are sometimes referred to by abbreviations. For example, CYP1A1 refers to cytochrome P450 1A1; CYP1A2 refers to cytochrome P450 1A2, and so forth. The term "P450 gene" includes genes that hybridize with known P450 genes under stringent conditions, or whose expression products specifically bind to antibodies against known P450 enzymes.

TABLE 1

Human Cytochrome P450s: Tissue distribution and carcinogen activation

| Family | Member | Tissues | Carcinogens* |
|--------|--------|---------|--------------|
| 1A | 1A1 | In, Li, Lu, Pla, Skin | B(a)P |
|    | 1A2 | Li | AAF, AF, AFB$_1$, IQ, MeIQ, NNK |
| 2A | 2A6 | Li, NE | AFB$_1$, DEN, DMN, NNK |
| 2B | 2B6 | Li | AFB$_1$, NNK |
|    | 2B7 | Li, Lu | AFB$_1$ |
| 2D | 2D6 | Li | NNK |
| 2E | 2E1 | Li, Lu, In | DEN, DMN, NNK |
| 3A | 3A3, 3A4 | Li, Lu, In | AFB$_1$, AFG$_1$, B(a)P7, 8-diol |

B(a)P, Benzo (a) pyrene:
AAF, acetylaminofluorene;
AF, aminofluorene;
IQ, 2-amino-3-methylimidazo(4,5-f)quinoline;
MeIQ, 2-amino-3,4-dimethylimidazo(4,5-f)quinoline;
DEN, N-nitrosodiethylamine;
DMM, N-nitrosodimethylamine;
AFB$_1$, aflatoxin B$_1$;
AFG$_1$, aflatoxin G1;
B(a)P7, 8-diol;
NNK, 4-(methylnitro-samino)-1-3-pyridyl)1-butanone
Li, liver;
Lu, Lung;
In, intestine;
Pla, placenta;
NE, nasal epithelium.
*Carcinogens selected for the evaluation of the established cell lines.

Nucleotide substitutions, deletions, additions, and the like also may be incorporated into the cytochrome P450 DNA fragment to be cloned, so long as the biological function of the expression product is not substantially disrupted. (Maniatis, et al, *Molecular Cloning: A Laboratory Manual*, 2nd Ed. 1989 and Berger and Kimmel, *Methods in Enzymology*, Volume 152, *Guide to Molecular Cloning Techniques* (1987). The clones may be expressed or the P450 gene of interest can be excised or synthesized for use in other systems. The sequences of various cDNA isolates are described for cytochrome P4502C9 (Umbenhauer, et al., *Biochem.*, 26:1094–1099, 1987 and Kimura, et al., *Nucl. Acids Res.*, 15:10053–10054, 1987); P4502E1 (Song, et al., *J. Biol. Chem.*, 261:16689–16697, 1986 and Umeno, et al, *Biochem.*, 27:9006–9013, 1988); and P4503A4 (Beaune, et III. Expression Systems The cytochrome P450 genes can be transferred into the cell lines by transfection of plasmid DNA or by retroviral infection. The viral vector is preferably replication defective so that stable cell lines expressing P450 genes are obtained. Transfection of cells can occur through those methods commonly used, such as calcium or strontium phosphate treatment, microinjection, electroporation, or lipofection. For example, the cells may be infected with a molony-LTR driven promoter or a vaccinia virus or lipofected with an adenovirus-promoter, HIV-promoter or CMV-promoter construct. The transfected DNA plasmid can contain a selectable marker gene or be co-transfected with a plasmid containing a selectable marker, and in some cases, the retroviral vector contains a selectable marker gene. Where one or more selectable marker is transferred into the cells along with the P450 gene, the cell populations containing the P450 gene can be identified and enriched by selecting for the marker or markers. Markers typically are antibiotic resistant to such antibiotics as tetracycline, hygromycin, neomycin, and the like.

IV. Utility of Cell Lines

The immortalized, non-tumorigenic, stable, P450-expressing cell lines of the present invention are useful in the following respects.

(1) Identification of potential chemopreventive drugs. These cells are useful for screening chemicals suitable for the treatment of cancer and related diseases, by growing them in vitro in medium containing the chemical to be tested and then, after a suitable period of exposure, determining whether and to what extent genotoxicity, DNA adduct formation, mutagenicity, cell transformation and/or cytotoxicity has occurred following exposure to a carcinogen, e.g., by trypan blue exclusion assayor related assays (Paterson, *Methods Enzymol.*, 58:141, 1979), or by growth assays such as colony formatting efficiency (MacDonald, et al., *Exp. Cell. Res.*, 50:417, 1968), all of which are standard techniques well known in the art. Once a potential anticarcinogenic agent is identified, it and the cells can be used in further studies, such as drug design.

(2) Studies of the control of squamous differentiation, and identification of chemical and biological agents which induce squamous differentiation (bronchial cells only). This is accomplished by assays previously described for normal human bronchial epithelial cells (Masui, *Proc. Natl. Acad. Sci. U.S.A.*, 83:2438, 1986). Some cells retain the ability to undergo squamous differentiation in response to serum. Induction of terminal differentiation may be an effective way of controlling the growth of cancer. Chemical and biological substances are screened for their ability to induce differentiation by adding them to the growth medium of these cells and then after a suitable time interval determining whether a complex of changes including cessation of DNA synthesis and the appearance of squamous morphology has occurred. The cells are also useful for studies for the biological mechanisms of squamous differentiation, and the existence of both serum-resistant and serum-sensitive cell lines enables comparisons and identification of genes involved in the process of differentiation.

(3) Programmed cell death. The cell lines are also used for identifying agents that induce programmed cell death or apoptosis, which may have an important impact on prevention of malignant transformation. Programmed cell death is assayed by DNA fragmentation or cell-surface antigen analysis.

(4) Use of recombinant DNA expression vectors to produce proteins of interest. For example, the gene encoding a protein of therapeutic value may be recombined with controlling DNA segments (i.e. containing a promoter with or without an enhancer sequence), transferred into the cell (e.g., by strontium phosphate transfection) and then the protein produced may be harvested from the culture supernatant or a cellular extract by routine procedures well known in the art.

(5) Studies of metabolism of carcinogens and other xenobiotics. Carcinogens and other xenobiotics may be added to the growth medium of these cells and then the appearance of metabolic products of these compounds may be monitored by techniques such as thin layer chromatography or high performance liquid chromatography and the like.

(6) Studies of DNA mutagenesis. Substances known or suspected to be mutagens, or precursors of mutagens, may be added to the growth medium of the cells and then mutations may be assayed, e.g., by detection of the appearance of drug resistant mutant cell colonies (Thompson, *Methods Enzymol.*, 58:308, 1979). Similarly, cell-mediated DNA mutagenesis, by co-cultivating the cells with cell types known or suspected to be capable of secreting mutagenic compounds (Hsu, et al., *Proc. Natl. Acad. Sci. U.S.A.*, 75:2003, 1978).

The P450 enzyme can also be linked to a mutagen detection assay such as the Ames Salmonella/microsome system for detecting or testing the mutagenic frequency induced by environmental pollutants, carcinogens and the like (Ames, et al., *Mut. Res.*, 31:347, 1975). Other standard methods well known in the art such as chromosome aberration and sister chromatic exchange induction in Chinese hamster ovary cells (Galloway, et al., *Environ. Mutagen.*, 7:1, 1985) or mouse lymphoma cell mutagenesis assays (Myhr, et al., *Prog. in Mut. Res.*, 5:555–568, 1985) can, of course, also be used for testing mutagenicity.

(7) Studies of chromosome damaging agents. Substances known or suspected to cause chromosomal damage may be added to the culture medium of these cell lines, and then the extent of chromosomal damage may be measured by techniques such as measurement of the frequency of sister chromatic exchange (Latt, et al., In: Tice, R. R. and Hollaender, A. *Sister Chromatic Exchanges,* New York: Plenum Press, pp. 11 ff., 1984).

(8) Studies of malignant transformation. Chemical, physical and viral agents, and transferred genes including oncogenes, mutant tumor suppressor genes, and high molecular weight genomic DNA from-tumors are introduced into cells and malignant transformation is determined using standard assays such as anchorage independent growth or tumor formation in athymic nude mice.

(9) Screening for potential chemotherapeutic agents. Cells altered by transfer of oncogenes or chemical carcinogens (as in paragraph 7 above) are used to screen for chemotherapeutic agents by tests which examine reversion of the transformed phenotype of cells by reduction of 50 bb agar growth or reduced tumor formation in nude mice.

(10) Studies of cellular biochemistry. For example, changes in intracellular pH and calcium levels are correlated with cell growth and action of exogenous agents including, but not limited to, those described in paragraphs 1 through 9 above. To study intracellular pH and calcium levels, cells in suitable culture vessels are exposed to fluorescent indicator dyes and then fluorescence emissions are detected with a fluorescence spectrophotometer (Grynkiewicz, et al., *J. Biol. Chem.*, 260:3440–3450, 1985).

(11) Studies of cellular responses to growth factors and production of growth factors. The cells may be used to identify and purify growth factors important for growth and differentiation of human bronchial and liver epithelial cells. The cells of the present inventions are particularly useful for such an application since they grow in serum-free media. Therefore, responses to growth factors can be studied in precisely defined growth media and any factors produced by the cells may be identified and purified without the complication of the presence of serum.

(12) Studies of intracellular communication, e.g., by dye scrape loading assays. To determine whether the cells growing in vitro have the ability to communicate via gap junctions; the cultures may be scraped, e.g. with a scalpel in the presence of a fluorescent dye in the growth medium. Cells at the edge of the wound are mechanically disrupted and therefore take up dye; whether intercellular communication has occurred may be ascertained by determining whether cells distant from the wound also contain dye.

(13) Characterization of cell surface antigens. The cells are incubated with an antibody against the cell surface antigen of interest, and then reacted with a second antibody which is conjugated to a fluorescent dye. The cells are then evaluated using a fluorescence activated cell sorter to determine whether they are fluorescent and therefore possess the cell surface antigen.

(14) Hybrid studies for identification of tumor suppressor activity. To determine whether these cell lines contain tumor suppressor genes, they are fused to malignant tumor cells. The presence of tumor suppressor genes is indicated by loss of malignancy, e.g., as detected by loss of ability to form tumors in athymic nude mice, in the hybrid cells. See Stanbridge, et al., *Science*, 215:252–259, 1982.

(15) Identification of novel genes. Novel genes, including transforming genes in naturally occurring cancers described in paragraph 8 above, growth factor genes as described in paragraph 11 above, tumor suppressor genes as described in paragraph 14 above, using standard molecular biological techniques (Davis, et al., *Methods in Molecular Biology*, New York: Elsevier, 1986) and techniques such as cDNA subtraction cloning and the like. These genes or their derivatives can be used in gene therapy.

Of course, kits for screening carcinogenic or antineoplastic agents and for any other usage as described herein, are easily assembled, comprising container(s) containing the cell line(s) of the present invention, media for propagating cells, and reagents and/or apparatus for detecting morphological, physiological and/or genetic responses in the cell lines. Other components routinely found in such kits may also be included together with instructions for performing the test.

EXAMPLES

Example 1. Preparation of Immortalized Cells

A. Bronchial Cells

The immortalized human bronchial epithelial cell lines used in producing the cytochrome P450-transfected cells of the present invention are described in U.S. Pat. No. 4,885,238. These cell lines are prepared as follows.

Normal-human bronchial epithelial (NHBE) cells were cultured from explants of necropsy tracheobronchial specimens from noncancerous individuals as described by Lechner, et al., *J. Tissue Culture Methods*, 9:43–48, 1985. The NHBE cells were infected with adenovirus-12 SV40 hybrid virus. In all cases the life-span of these cultures was extended compared to NHBE; most of the cultures underwent a prolonged period of senescence referred to as "crisis." With continued culture, in some cases colonies of cells which had escaped senescence arose; such surviving colonies were subsequently passaged for extended periods of time and showed unlimited growth potential.

Like NHBE cells, but unlike bronchial carcinoma cells, some of the cell lines thus derived retained the capacity to undergo squamous differentiation in response to serum exposure. Injection of these cells into irradiated athymic nude mice did not result in formation of tumors after periods of up to nine months. Furthermore, these cell lines were found to be suitable recipients for transfection additional genes and useful for testing the cytotoxicity potential of chemical and physical agents, the growth inhibition or promoting capability of biological agents, and squamous differentiating potential of chemical and biological agents.

Development of the BEAS-2B Cell Line

A preferred cell line for use in this invention is BEAS-2B which was prepared as follows. NHBE cells were cultured from explants of autopsy specimens from noncancerous individuals as described by Lechner, et al., *J. Tissue Culture Methods*, 9:43–48, 1985. The cells were cultured in a serum-free medium, LHC-9, harvested by trypsinization and seeded in 10 ml growth medium into 100 mm culture dishes (Lux, Miles Scientific, Naperville, Ill.) whose growth surfaces had been coated with a solution of bovine serum albumin, fibronectin and collagen (Lechner, et al., supra.).

Adenovirus 12-SV40 (Ad12SV40) hybrid virus (Schell, et al. *Proc. Natl. Acad. Sci. U.S.A.* 55:81–88, 1966) was grown in Vero cells as described by Rhim, et al., *Proc. Natl. Sci, U.S.A.*, 78:313–317, 1981. NHBE cells were exposed to the virus at 37° C. for four hours at a multiplicity of infection of approximately 100. When the cultures reached confluence, each dish was subcultured into two 75 $cm^2$ flasks. The cells were allowed to reach confluence again and then were re-fed twice weekly until transformed colonies appeared and the normal cells senesced. Senescence of the normal cells was accelerated by exposing the cultures to 1% FCS in LHC-9 for 28 days (Lechner, et al., *Differentiation*, 25:229–237, 1984); all subsequent culture of these cells was in serum-free LHC-9 medium. Individual colonies were subcultured 41 days after the viral infection and cell strains thus derived from this experiment were designated BEAS-2B. Northern blots of BEAS-2B cells have shown that these cells express phase II enzymes epoxide hydrolase, catalase, glutathione peroxidase, superoxide dismutase and glutathione S-transferase.

When supplemented with exogenous cytochrome P450s, BEAS-2B cells represent an authentic model system for analysis of normal lung tissue in vivo. BEAS-2B cells, are derived from human bronchial epithelial cells, which are the likely progenitor cells of all types of lung cancer. Moreover, except for cytochrome P450s, which are expressed at reduced levels or absent, the BEAS-2B cells express many enzymes involved in the activation process of carcinogens and mutagens, such as glutathione S-transferase, epoxide hydrolase, NADPH cytochrome P450 reductase. BEAS-2B cells have been deposited under the terms of the Budapest Treaty at the American Type Culture Collection and assigned the accession number CRL9609.

B. Liver Cell Lines

The preparation and properties of immortalized, nontumorigenic, human liver cell lines (before transfection with exogenous P450 genes) are discussed in some detail in copending application, U.S. Ser. No. 07/844,873. Pertinent details of the preparation of cell lines are also described below. Properties of the cell lines are summarized.

(1) Preparation
(a) Primary culture of normal adult liver tissue

LCM medium (Lechner, J. F. et al., *Cancer Detect. Prev.* 14:239 (1989)) consists of PFMR-4 medium (Biofluids, Rockville, Md.) wherein the $Ca^{2+}$ concentration is reduced to 0.4 mM and arginine is replaced with 0.3 mM ornithine, supplemented with insulin (1.45 μM), transferrin (125 nM), cholera toxin (300 pM), epidermal growth factor (825 pM), hydrocortisone (0.2 μM), triiodothyronine (10 nM), retinoic acid (10 nM), phosphoethanolamine (0.5 μM), Ex-Cyte V (312 μM), bovine pituitary extract (7.5 μg protein/ml), and chemically denatured serum.

To make LCM medium conditioned by Hep-G2 cells (HGLCM), Hep-G2 cells (American Type Culture Collection, Rockville, Md.) were maintained in DMEM medium supplemented with 10% fetal bovine serum. Near-confluent cultures of such cells were washed twice with LCM and then maintained in LCM for 72 hours. The supernatant medium (HGLCM) was removed, sterilized by filtration through a 0.22 μm membrane and stored under sterile conditions.

Normal liver epithelial cells were obtained by collagenase/dispase perfusion of the left lower lobe of livers from immediate autopsy adult donors with no clinical evidence of cancer (Hsu, I. C. et al., *In Vitro Cell Develop. Biol.* 21: 154 (1985)). Cultures were inoculated into flasks that had been precoated with collagen I (Vitrogen™, Celtrix Laboratories, Palo Alto, Calif.) and incubated overnight in Waymouth's medium containing 10% fetal bovine serum. The following day, the cultures were rinsed with phosphate buffered saline (PBS) and the medium was changed to HGLCM.

Within 2 to 4 days of isolation of the normal cells, groups of randomly spaced replicating cells with an epithelial-like morphology were evident. These cultures formed a confluent monolayer after 10–14 days of incubation. These normal cells could be subcultured at a 1:4 split ratio using the same collagenase/dispase solution as was used in establishing the primary culture to remove the cells from the surface of the culture vessel. The average lifespan of these normal liver epithelial cell cultures was 12 population doublings.

(b) Production of the SV40 Tag-expressing retrovirus

A recombinant retrovirus carrying the large T antigen gene of SV40 was constructed by insertion of BgIII-HpaI fragment of the SV40 viral DNA (nucleotides 5235–2666) into the BamHI site of the pZipNeoSVX (Jat., P.S. et al., *Mol. Cell. Biol.* 6:1204 (1986)) retroviral vector, using BamHI linkers and standard recombinant DNA techniques. The fragment of the SV40 genome employed lacked both the early promoter and the polyadenylation site.

Infectious recombinant virus particles were made by infecting the amphotropic packaging cell line PA317 with the ecotropic recombinant virus established by transfecting the vector obtained above into the ecotropic packaging line Psi2. Transfected cells were isolated by neomycin selection and 10 clones were isolated. The cloned PA317 cells were propagated in DMEM medium supplemented with 10% FBS. The medium was changed to serum-free PC-1 medium (Ventrex Laboratories, Portland, Me.) and collected virus was titered by infecting $8=10^4$ NIH 3T3 cells in a 60 mm dish with various dilutions of the supernatant medium containing virus in the presence of 8 μg/ml polybrene and counting the colonies after 10 days of selection using 750 μg/ml of neomycin.

(c) infection of primary liver tissue culture cells

A pool of virus from 7 of the 10 clones of the transfected PA317 cells was used to infect the primary liver tissue cultures. $8=10^4$ cells of the primary cultures were infected with the recombinant virus for 2 hours in the presence of 8 μg/ml polybrene in PC-1 medium. After the infection, the cultures were washed with HEPES buffered saline (HBS) and incubated in LCM medium. Infection with the recombinant virus caused virtually all of the liver cells in the culture to undergo rapid division. Several cultures have been so established. All of these have been passaged as mass cultures. Initially, the THLE cells underwent approximately 25 population doublings during the first six weeks post-infection, then growth decreased markedly. Cells were cryopreserved at each passage during this early growth period.

The THLE-2 cell line was deposited under the terms of the Budapest Treaty at the American Type Culture Collection, 12301 Parklawn Dr., Rockville, Md., on May 16, 1989 and assigned the accession number CRL 10149. The THLE-3 cell line was deposited under the terms and conditions of the Budapest Treaty at the American Type Culture Collection on Jan. 14, 1993 and was assigned the accession number CRL 11233. The THLE-5 cell line (also sometimes referred to as "THLE-5B") was deposited under the terms and conditions of the Budapest Treaty at the American Type Culture Collection on Apr. 23, 1992, and was assigned the accession number CRL11113. The THLE-5B cell lines was used in many of the experiments in Examples 2–5.

(2) Properties of THLE cell lines

Transforming DNA. THLE cells contain approximately one copy of the SV40 T antigen gene as determined by Southern blotting.

Immortality. Growth decreased markedly after ≈25 PDs during the first 6 weeks after infection. At this time early-passage-cryopreserved THLE cells were used to determine the growth responses to LCM medium supplements. The clonal growth rate could be optimized by omitting lipid (ExCyte V) and cholera toxin supplements, replacing ornithine with arginine, and replacing HepG2-conditioned medium with T2-CM. With this modified growth medium (MLCM), THLE cells have undergone >130 Pds with no evidence of senescence. Their apparent maximal PD time is 24 hour, and their colony-forming efficiency is ≈15%.

Expression of Hepatocyte Phenotypic Traits. Cytokeratin 18, but not cytokeratin 19, was uniformly expressed in early-passage THLE cells, whereas at passage 10–12, all cells also expressed cytokeratin 19. α-Fetoprotein or factor VIII expression was not detected at early- or late-cell passages, whereas $\alpha_1$-antitrypsin and $\alpha_2$-macroglobulin were present. Albumin was readily detected in the cytoplasm of early-passage THLE cells by immunocytochemistry. Islands of albumin-positive cells were surrounded by clusters of less intensely staining cells, indicating different cell clones or types. Immunoblot analyses showed that late-passage THLE cells can secrete albumin. The albumin secretion by THLE cells was between ≈300 pg/ml and 14.5 ng/ml. γGT was weakly positive by cytochemistry in some colonies of THLE cells, as well as in the primary cultures before introduction of SV40 T antigen. In the same test 3T6 cells were negative, whereas HepG2 cells exhibited high enzyme activity.

Karyotype and Tumorigenicity Analysis. Karyotype analysis showed that THLE cells are hypodiploid with most karyotypes being near-diploid. Typical SV40 T antigen effects were also detected in THLE cells at passage 22—i.e., monosomy of chromosomes 13 and deletions of chromosomes 2 and 8. When the cell lines were tested for tumor formation by s.c. injection of $10^6$ cells per athymic nude mouse (20 animals), no tumors were found after 12 months of observation.

Metabolic Studies. The metabolism, cytotoxicity, and DNA adduct formation of three different chemical classes of carcinogens were investigated in THLE cells. $AFB_1$, B[a]P, or DMN caused dose-dependent cytotoxicity of THLE cells, suggesting metabolic activation of these promutagens to genotoxic metabolites. $AFB_1$, DMN, or B[a]P formed 3.5±0.9, 30.4±3.9, and 1.5±0.1 fmol of adduct per μg of DNA, respectively, in THLE cells grown in roller bottles. The major adduct found in cells treated with $^3$H-labeled B[a]P was chromatographically indistinguishable from the major product formed when (±)%7, t-8-dihydroxy-c-9,10-epoxy-7,8,9,10 -tetrahydrobenzo[a]pyrene (BPDE) was allowed to react with DNA. $^{32}$P-postlabeling analysis revealed the $N^1$-methyldeoxyguanosine adduct in THLE cells incubated with DMC. The major adduct in $AFB_1$-exposed THLE cells was 8,9-dihydro-8-(2,6-diamino-4- oxo- 3,4-dihydropyrimid-5-yl-formamido)-9-hydroxyaflatoxin $B_1$ (AFB$_1$-FAPyr), whereas AFB$_1$-diol and 8,9-dihydro-8(N$^1$-guanyl)-9 -hydroxyaflatoxin $B_1$ were minor adducts. Preincubation of cells with Aroclor 1254, an inducer of CYP1A1/1A2 enhanced formation of B[a]P-related adducts 3-fold to 4.9±2.7 fmol/μg of DNA, decreased DMN-related adducts to 3.4±0.1 fmol/μg of DNA, and did not affect AFB$_1$-DNA adduct formation (1.6±0.4 fmol/μg of DNA). Pretreatment with β-naphthoflavone abolished the ability of THLE cells to activate B[a]P. Similarly, ethanol treatment of the THLE cells decreased metabolic activation of DMN.

Expression of Phase I and II Enzymes. RNA analyses of CYP1A1 mRNA steady-state levels were consistent with the results from DNA-adduct analyses. CYP1A1 mRNA was undetectable in control cells grown as roller bottle cultures. Aroclor 1254 or B[a]P exposure increased steady-state levels of CYP1A1 mRNA. When cells were treated with both agents, the CYP1A1-inducing effects with both components appeared additive. In contrast, neither DMN nor AFB$_1$ induced expression of CYP1A1 mRNA in roller bottle cultures of THLE cells. Other CYPs (CYP1A2, CYP2A3, CYP2E1, CYP2D6, and CYP3A4) were not detectable by RNA blot analysis.

THLE cells express the same amount of epoxide hydrolase mRNA but less NADPH CYP reductase mRNA. Detoxifying enzymes such as superoxide dismutase, catalase, and glutathione peroxidase are expressed in THLE cells at mRNA steady-state levels similar to the amounts found in human liver tissue. GST πmRNA were not found in the donor's liver tissue but were expressed by THLE cells. In contrast, GST-α mRNA was only detected in the original human tissue (data not shown).

Conclusions. These results indicate that THLE cell lines exhibit many of the properties associated with the quiescent state of normal adult hepatocytes, other than the expression of a full complement of cytochrome P450 enzymes. Although THLE cells are capable of some metabolism of toxic, carcinogenic or mutagenic substances, this capacity is much less than that of the P450-transfected THLE cells of the present invention. See Example 5.

Example 2. Introduction of P450 Enzymes into Immortalized Cells

A. pXT1 Defective-Retrovirus Infection System cDNAs for the cytochrome P450 enzymes, 1A2, 2A3, 3D6, 2E1, and 3A4, were introduced by recombinant high titer amphotropic retroviruses into the BEAS-2B cells. These retroviruses were generated by cloning the corresponding cDNAs into a plasmid pXT1 (Boulter, et al., *Nucleic Acid,* 15:7194, 1987) and transfecting the recombinant plasmids into co-cultured packaging lines with amphotropic (PA317) and ecotropic envelopes (Psi2) using calcium phosphate precipitation (Bestwick, et al., *Proc. Natl. Acad. Sci. U.S.A.,* 85:5404–5408, 1988) (see FIG. 1).

After 10 days, virus was collected from confluent PA317/Psi2 cultures in serum free PC-1 medium (Ventrex Laboratories, Inc., Portland, Oreg.). The titers were determined on NIH3T3 cells and were expressed as neomycin resistant colonies/ml supernatant. The BEAS-2B cells were infected for 2 hours with the P450 viruses or the control virus, pXT1, in PC-1 medium supplemented with 8 μg/ml polybrene (Table 2).

TABLE 2

| Generation of high titer amphotropic P450 retroviruses | | |
|---|---|---|
| Retrovirus | Titer | Metabolic Activity |
| 1A2 | $10^5$ | AA, HAA, MeiQ, NNK, AFB$_1$, caffeine |
| 2A3 | $2 \times 10^5$ | DEN, DMN, NNK, AFB$_1$, coumarin |
| 2D6 | $5 \times 10^4$ | buforol, debrisoquine, NNK |
| 2E1 | $10^5$ | DEN, DMN, NNK, Ethanol |
| 3A4 | $6 \times 10^4$ | AFB$_1$, B(a)P 7,8-diol, nifedipine |

AA, aromatic amines;
HAA, heterocyclic aromatic amines;
NNK, 4-(methyl-nitrosamino)-1-(3-pyridyl)-1-butanone;
AFB$_1$, aflatoxin B$_1$;
DEN, diethylnitrosamine;
DMN, dimethylnitrosamine;
MeiQ, 2-amino-3,8-dimethylimidazo[4,5-f]quinoxaline.

An equal ratio of cells to colony forming units of the virus was employed. Forty-eight hours after infection the BEAS-2B cells were selected for G418 neomycin resistance with 125 μg/ml neomycin for 8 days. Subsequently, the cells were selected for the presence of the introduced genes by Western blot analysis. Exemplified for BEAS-2B-1A2, the population and 3 clones (clone 8>clone 3>clone 6) expressed the protein corresponding to the respective P450 retrovirus. In accordance, clone 8 (cl 8) showed the highest sensitivity being up to 150 times more responsive to the cytotoxic effect and up to 250 times to the genotoxic effect of a model compound, AFB1, than the control.

Figure 2:
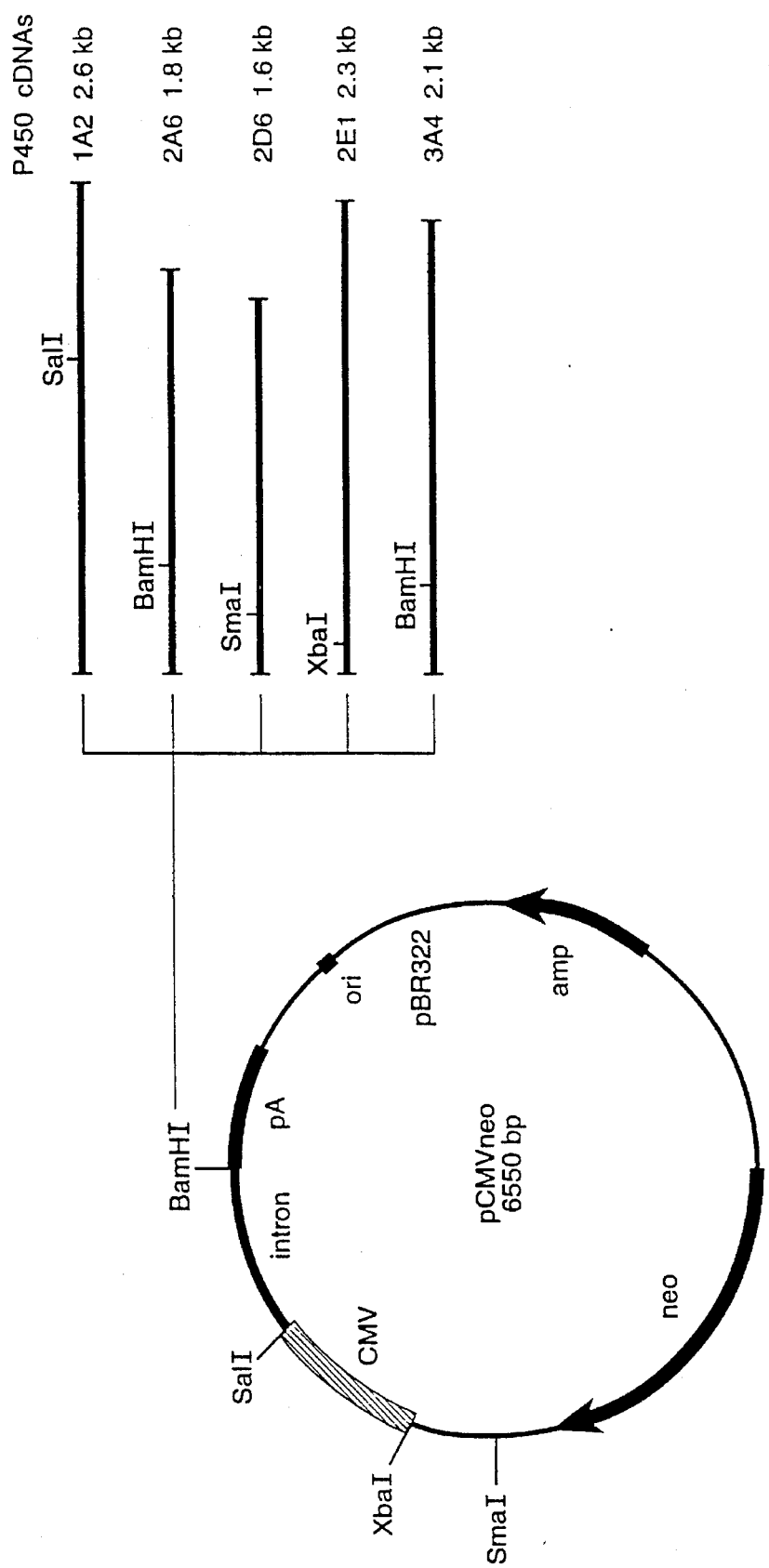
FIG. 2 shows a map of the pCMV and cytochrome P450 fragments for insertion into this vector.
Figure 3:
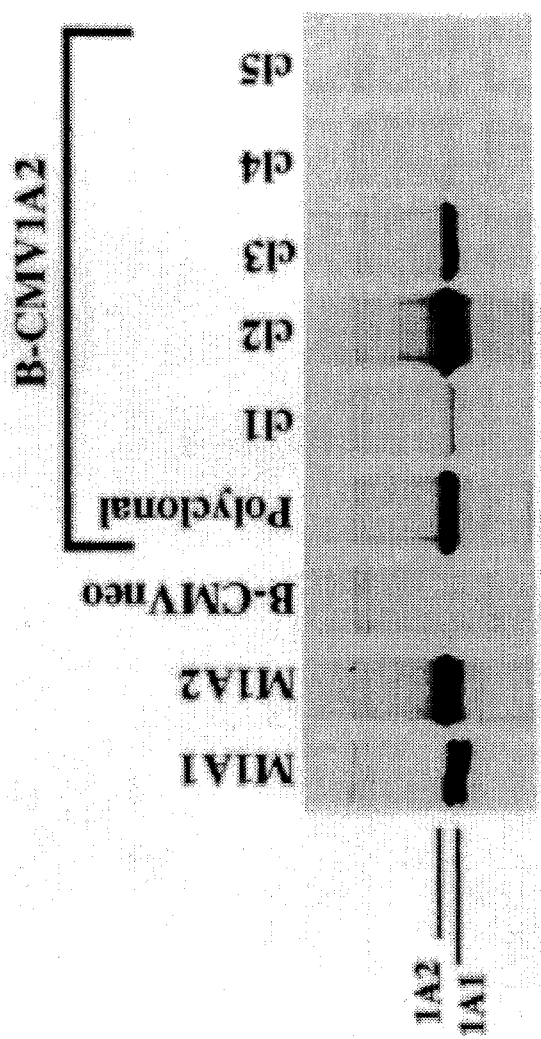
FIG. 3 shows a Western blot of BEAS-2B-CMV-1A2 cells confirming expression of CYP1A2 in these cells. Abbreviations: B=BEAS-2B, cl=clone, m=microsomal.

B. CMV-Plasmid Lipofection System pCMV-cytochrome-P450 constructs were generated by cloning human cytochrome P450 cDNAs at the 3' side of the promoter of the cytomegalovirus (CMV) immediate-early gene region. See FIG. 2. cDNA fragments were inserted into the BamHI site (after modifications of the sticky ends) of the pCMV neo plasmid (kindly provided by Bert Vogelstein, Johns Hopkins University) to generate the pCMV-cytochrome P450 constructs. Construction of pCMV is described by Baker et al., *Science* (1990) 249: 912–915. pA is the polyadenylation sequence of the rabbit β-globin gene. Neo is the selectable neomycin gene, conferring G418 selection resistance. Amp$^R$ is ampicillin resistance gene.

pCMV-cytochrome-P450 constructs (and unmodified pCMV vector as a control) were introduced into liver and bronchial cell lines by lipofection. Briefly, 1.10$^6$ cells were lipofected with 10 μg DNA in 5 ml of Opti-MEM medium (GIBCOBRL) containing 50 μl of Lipofectin (GIBCO-BRL). After 3 hours the cells were washed and fresh medium containing 10% chemically denatured fetal bovine serum (Upstate Biotechnology, Inc., New York) was added. After 48 hours the transfected THLE-5B or BEAS-2B cells were selected for G418 resistance with 50 μg/ml G418 for two weeks.

Example 3. Immunoblot Analysis of Introduced P450 Genes

Figure 8:
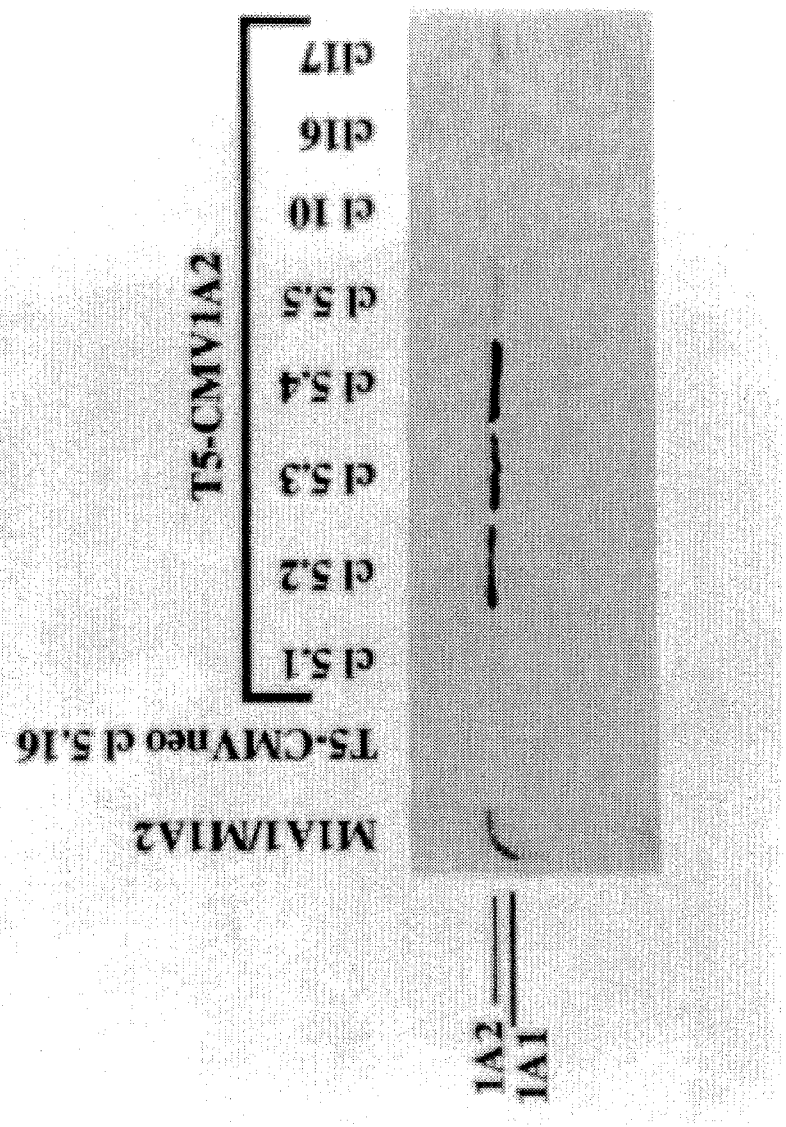
FIG. 8 shows a Western blot of THLE-5B-CMV-1A2 cells confirming expression of CYP1A2 in these cells. Abbreviations: T=THLE-5B.
Figure 9:
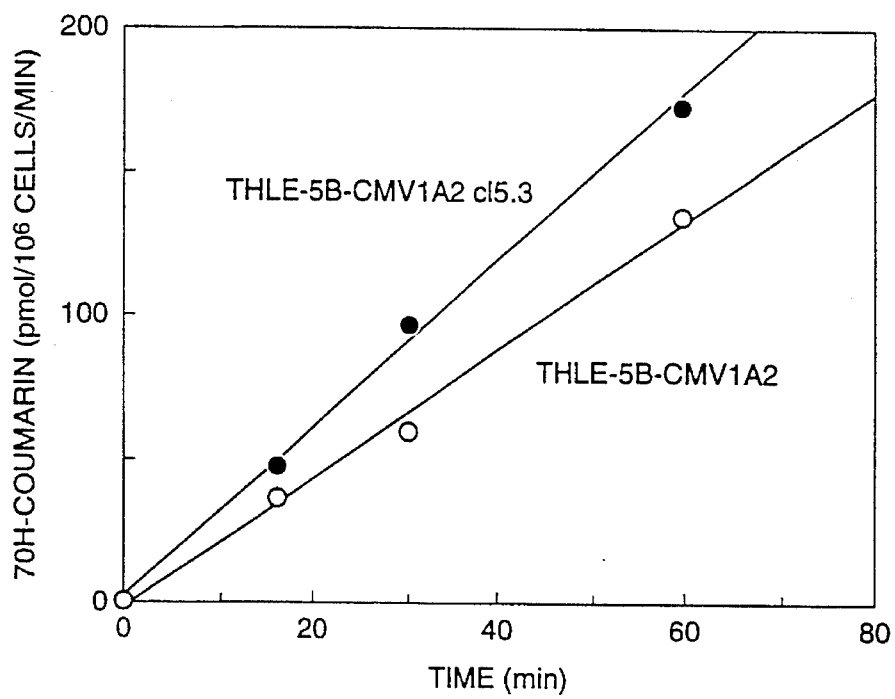
FIG. 9 shows a time course of ethoxycoumarin O-deethylase activity in THLE-5B-CMV-1A2 cells.

After introduction of the P450 genes by replication-defective retroviral infection or lipofection, as described in Example 2, cell lines were tested for expression of P450 genes by Western blotting. Samples of total protein extract (approximately 2.10$^4$ cells) and standard human cytochrome P450 microsomal fractions (10 μg) (Gentest Corp., Woburn, Mass.) (as positive controls) were subjected to SDS-PAGE (15% polyacrylamide gels) and transferred to nitrocellulose membranes using a semi-dry electroblotter (Ancos, Denmark). The filters were incubated with polyclonal antibodies against the cytochrome P450 cytochrome under test (diluted 1:50) and developed using an ImmunoPure ABC alkaline phosphatase rabbit IgG staining kit (Pierce, Socochim SA, Switzerland). FIGS. 3–7 show expression of P450 cytochromes 1A2, 2A6, 3A4, 2E1 and 2D6 in respective BEAS-2B cells that have been transfected with the respective gene linked to the pCMV vector. Also shown are standard microsomal fractions (M) as positive controls and BEAS-2B cells transfected with unmodified pCMV (B-CMV-neo) as negative controls. These results indicate that transfected exogenous P450 cytochrome genes are expressed in BEAS-2B cells. Similar results were obtained after transfected of THLE-5B cells. FIG. 8 shows that expression of cytochrome P450-1A2 was obtained in THLE-5B-CMV 1A2 cell lines. No expression was observed in control THLE-5B-CMV cells (which lack an exogenous P450 gene).

Figure 4:
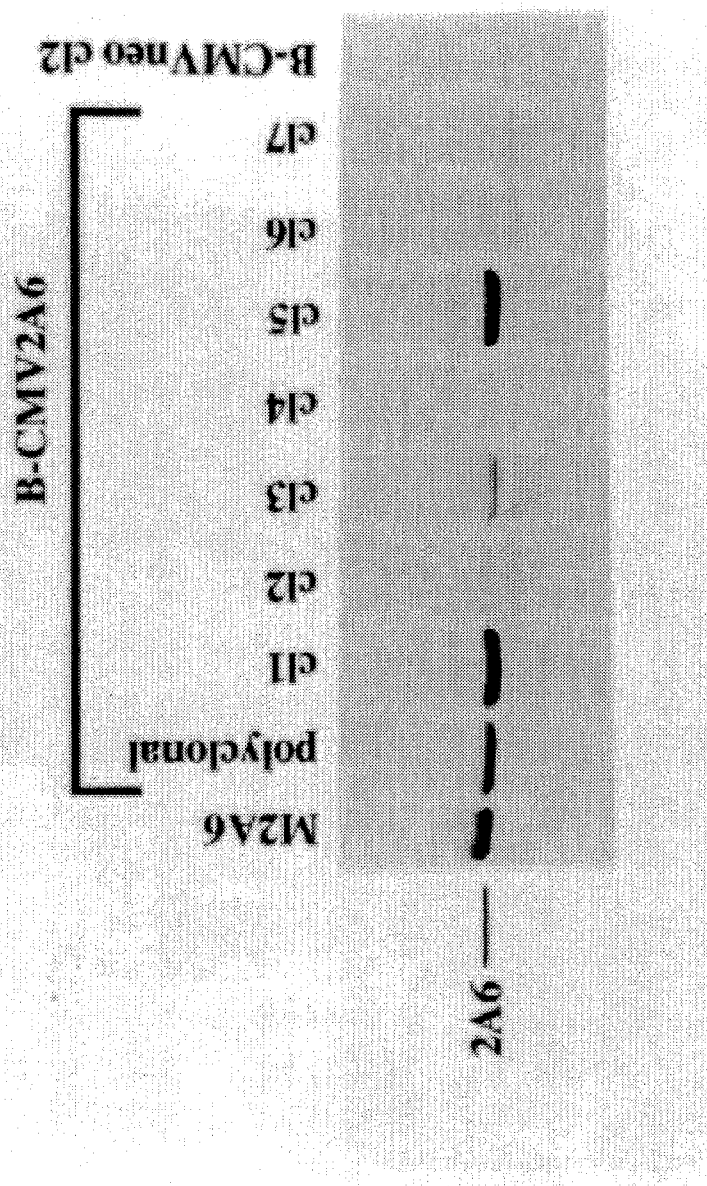
FIG. 4 shows a Western blot of BEAS-2B-CMV-2A6 cells confirming expression of CYP2A6 in these cells.
Figure 5:
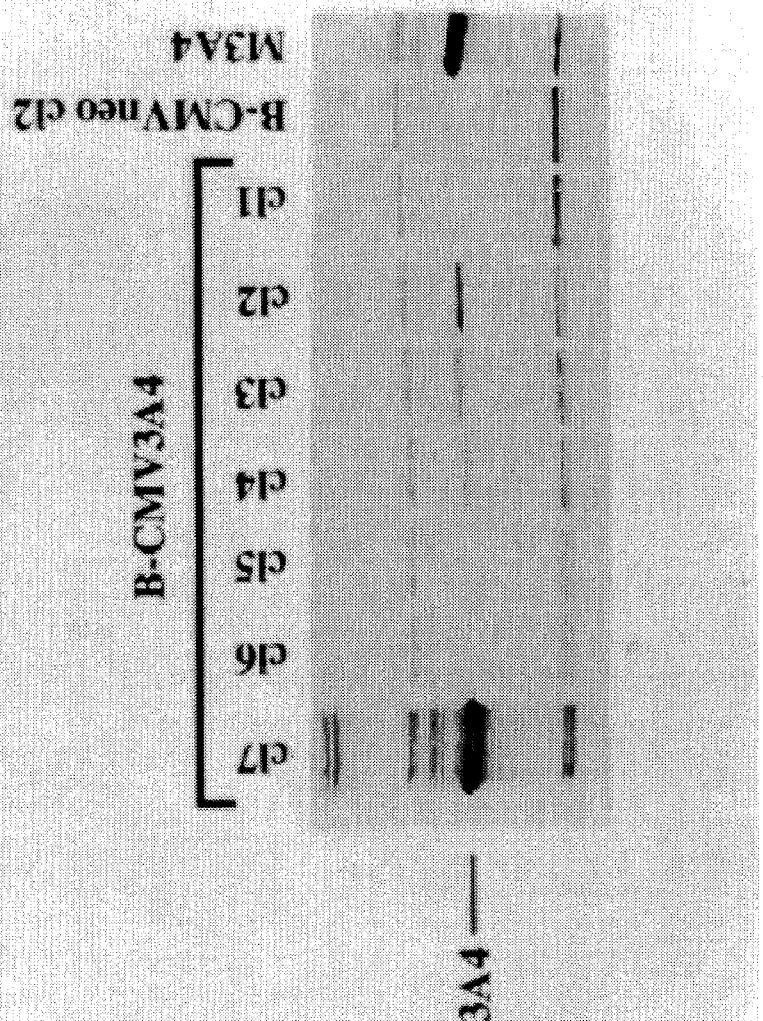
FIG. 5 shows a Western blot of BEAS-2B-CMV-3A4 cells confirming expression of CYP3A4 in these cells.
Figure 6:
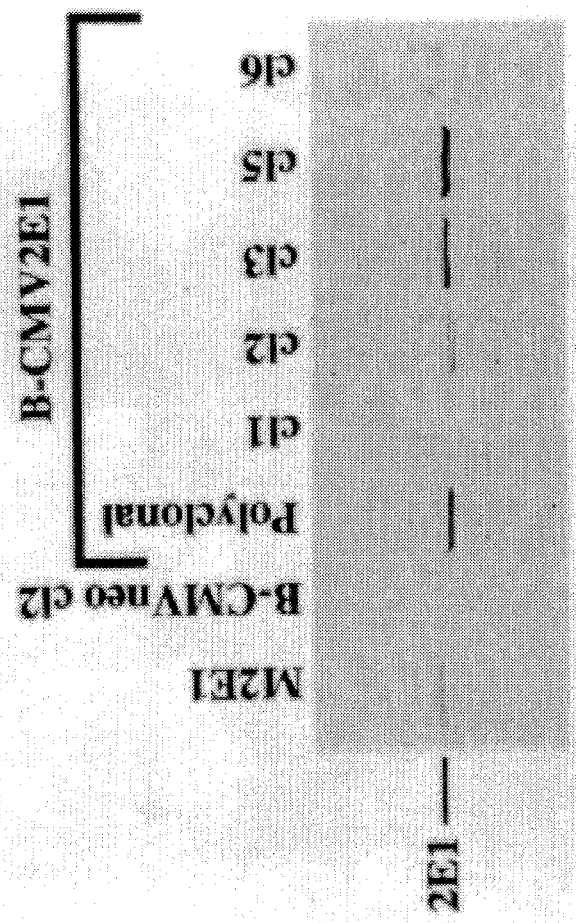
FIG. 6 shows a Western blot of BEAS-2B-CMV-2E1 cells confirming expression of CYP2E1 in these cells.
Figure 7:
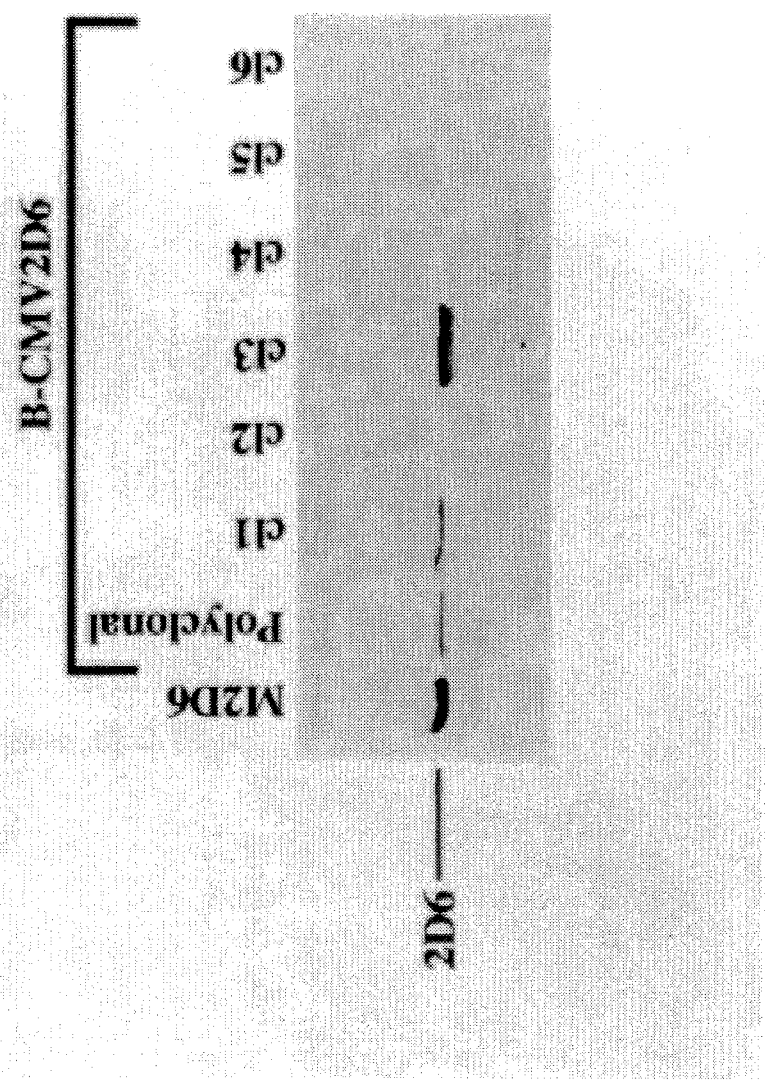
FIG. 7 shows a Western blot of BEAS-2B-CMV-2D6 cells confirming expression of CYP2D6 in these cells.

Example 4. Metabolism of Cytochrome P450 Substrates in Cells Transfected with Exogenous P450 Genes Cells containing exogenous P450 genes were tested for their ability to metabolize P450 substrates thereby demonstrating the functionality of P450 enzymes resulting from expression of the exogenous genes. In one experiment, ethoxycoumarin was used as a substrate to determine functionality of cytochrome P450 1A2 in BEAS-2B and THLE-5B cells. Cultures were plated at 0.25 to 0.5 $10^6$ cells/60-mm petri dish. On the next day, the medium was replaced with 2 ml of assay buffer (0.2M sucrose, 0.05M Tris, pH 8.5, 0.01M $MgCl_2$) containing 250 µM 7-ethoxycoumarin substrate. After incubation at 37° C. for the desired length of time, 1.0 ml of the supernatant was acidified by the addition of 100 µl of 20% TCA. After centrifugation, the supernatant was mixed with 2.0 ml of 1.6M Glycine-NaOH buffer pH 10.3 and the fluorescence read with excitation at 390 nm and emission 440 nm. Quantitation can be achieved by comparison to the fluorescence of known quantity of umbelliferone. Table 3 shows ECD activity for AHH-1A2/Hyg (lymphoblast cell line containing CYP1A2, described by Crespi, supra), BEAS-2B-1A2 c18 (BEAS-2B cell line containing CYP1A2 linked to the pXT1 expression system), BEAS-2B-CMV-1A2 c12 (BEAS-2B cell line containing CYP1A2 linked to the pCMV expression system) and THLE-5B-CMV-1A2 c15.3 and THLE-5B-CMV-1A2 c15.4 (different clones of THLE-5B cells containing CYP1A2 cytochrome linked to the pCMV vector. FIG. 4 shows a time course for ECD activity of CYP1A2 for the THLE-5B-CMV-1A2 c15.3 and THLE-5B-CMV-1A2 c15.4 cell lines.

TABLE 3

Ethoxycoumarin O-deethylase activity in CYP1A2 expressing cells

| | ECD activity (pmol/$10^6$ cells/min) |
|---|---|
| AHH-1A2/Hyg | 1.25 |
| BEAS-2B-pXT1 cl4 | und. |
| BEAS-2B-1A2 cl8 | 0.07 |
| BEAS-2B-CMV-neo cl2 | und. |
| BEAS-2B-CMV-1A2 cl2 | 0.21 |
| THLE-5B-CMV-neo cl5.16 | und. |
| THLE-5B-CMV-1A2 cl5.3 | 4.3 |
| THLE-5B-CMV-1A2 cl5.4 | 2.0 | und., undetectable

In a similar experiment, it was also shown that THLE-5B-CMV-1A2 c15.3 cells are capable of metabolizing ethoxyresofurin substrate about 100-fold more rapidly than THLE-5B-CNV-neo c15.16 control cells. See Table 4. This confirms that the CYP1A2 enzyme resulting from expression of the exogenous gene is also functional for ethoxyresofurin metabolism.

TABLE 4

Ethoxyresorufin-O-deethylase (EROD) activity in CYP1A2-expressing THLE cells

| Cell lines | EROD activity in whole cells* |
|---|---|
| T5-CMV-neo cl5.16 | 0.11 ± 0.04 |
| T5-CMV-1A2 cl5.3 | 9.90 ± 0.40 |

*pmol/$10^6$ cells/min

In a further experiment, it was shown that BEAS-2B cells containing exogenous cytochrome P450 2A6 are able to metabolize coumarin at a high rate compared with control cells, indicating functionality of the 2A6 expression product. See Table 5.

TABLE 5

Coumarin-7-hydroxylase (CH) activity in CYP2A6-expressing BEAS-2B

| Cell lines | CH-activity in whole cells* |
|---|---|
| B-CMV-neo cl2 | und. |
| B-CMV-2A6 cl1 | 45.7 ± 3.3 |
| B-CMV-2A6 cl3 | 2.0 ± 0.7 |
| B-CMV-2A6 cl5 | 37.0 ± 2.7 |

*pmol/$10^6$ cells/min.; und., undetectable

Example 5. Cytotoxicity and Genotoxicity Analysis of P450-expressing Cell Lines

A. $AFB_1$ Cytotoxicity Analysis

Cultures were exposed to the indicated concentrations of Aflatoxin $B_1$ ($AFB_1$). Each culture contained about $1 \times 10^5$ cells per 60 mm dish. After 28 hours, the cells were washed and fresh medium was added. After 5 days the cell number was determined. Cytotoxicity is expressed as survival relative to the corresponding untreated cells. Values are expressed as the mean ±SD of two independent experiments.

Figure 10:
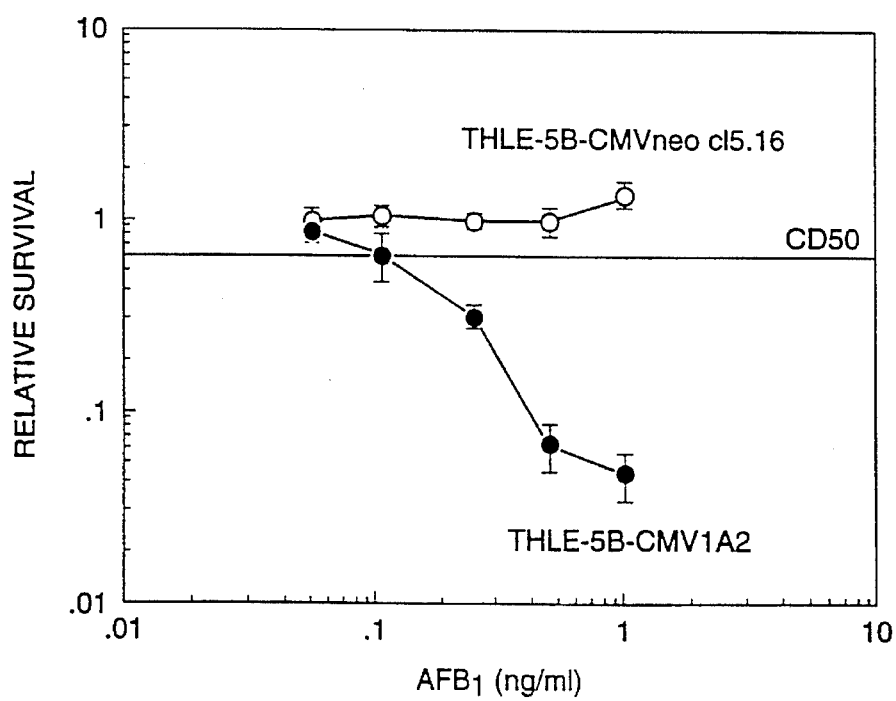
FIG. 10 shows the cytotoxicity of Aflatoxin $B_1$ in THLE-5B-CMV-1A2 and THLE-5B-CMV-neo lines.

Table 6 and FIG. 10 compare the relative survival of different cell types after treatment with various dosages of $AFB_1$. AHH-1A2/Hyg is the P450-expressing lymphoblast cell line of Crespi, supra, and AHH-1TK+/− is a control lacking an exogenous P450 gene; BEAS-2B-1A2 c18 and BEAS-2B-CMV-1A2 c12 are BEAS-2B cell lines containing an exogenous P450 gene under the respective control of pXT1 and pCMV expression systems; BEAS-2B-pXT1 c14 and BEAS-2B-CMV-neo c12 are control BEAS-2B cell lines containing unmodified pXT1 and pCMV expression vectors; THLE-5B-CMV-1A2 c15.3 is a THLE-5B line containing CYP1A2 on a pCMV vector, and THLE-5B-CMV-neo c15.16 is a control THLE-5B cell line containing an unmodified pCMV vector. The survival of THLE-5B strains was also determined by a 96-well microtiter assay. In this assay $1 \times 10^4$ cell/well were treated with $AFB_1$ for 28 hours. Four to five days, later the cells were stained with crystal violet. After dye extraction, the plates were read at 630 nm.

TABLE 6

AFB$_1$ cytotoxicity and ECD activity in 1A2-expressing cells

| AFB$_1$ (ng/ml) | AHH-1 TK+/− | 1A2/Hyg | B-pXT1 cl4† | B-1A2 cl8 | B-CMV-neo cl2 | B-CMV 1A2 cl2 | T5-CMV-neo cl5.16‡ | | T5-CMV-1A2 cl5.3 | |
|---|---|---|---|---|---|---|---|---|---|---|
| | Relative cell number | | Relative cell number | | | | Relative cell number | | | |
| | | | | | | | 0 6 cm* | 86 wells** | 0 6 cm | 96 wells** |
| 0.05 | nd | nd | nd | nd | nd | nd | 1.05 | 1.03 | 0.96 | 1.04 |
| 0.10 | nd | nd | nd | nd | nd | nd | 0.91 | 1.07 | 0.61 | 1.02 |
| 0.25 | nd | nd | nd | nd | nd | nd | 0.91 | 1.10 | 0.26 | 0.77 |
| 0.5 | nd | nd | nd | nd | nd | nd | 0.82 | 1.07 | 0.07 | 0.39 |
| 1.0 | nd | nd | nd | nd | nd | nd | 1.00 | 1.20 | 0.03 | 0.15 |
| 3.0 | nd | 0.76 | nd | nd | nd | nd | nd | nd | nd | nd |
| 5.0 | nd | nd | nd | nd | 0.98 | 0.52 | 1.08 | nd | nd | nd |
| 10.0 | nd | 0.69 | 1.04 | 1.01 | 1.19 | 0.37 | 1.04 | 0.89 | nd | nd |
| 50.0 | nd | nd | nd | nd | 1.03 | 1.19 | 0.83 | nd | nd | nd |
| 60.0 | 1.05 | 0.26 | nd | nd | nd | nd | nd | nd | nd | nd |
| 100.0 | nd | nd | 0.87 | 0.27 | 0.87 | 0.16 | 0.75 | 0.70 | nd | nd |
| 300.0 | nd | nd | nd | nd | nd | nd | nd | nd | nd | nd |
| 1000 | 0.89 | nd | 0.76 | 0.003 | 0.45 | 0.04 | 0.06 | nd | nd | nd |
| 10000 | 0.52 | nd | 0.13 | 0 | nd | nd | nd | nd | nd | nd |

†As used in this heading, "B-" refers to "BEAS-2B-"
‡As used in this heading, "T5-" refers to "THLE-5B"
0 6 cm*: 1.10$^5$cells/0 6 cm were treated with AFB$_1$ during 28 hrs. 5 days later the cells were counted.
96 wells: 1.10$^4$ cells/well treated with AFB$_1$ during 28 hrs. 4 to 5 days later the cells were stained with violet cristal. After elution, the plates were read at 630 nm.

Table 6 shows that all of the cell lines containing an exogenous p450 gene exhibited lower survival than the corresponding controls. The table also indicates that BEAS-2B cells expressing P450 from pCMV are more sensitive than BEAS-2B cells expressing P450 from pXT1, suggesting that operable linkage of a P450 gene to the cytomegalovirus promoter in pCMV supports greater expression of P450. Of the various cell lines tested, the THLE-5B cells containing P450 linked to the pCMV expression system showed the greatest sensitivity to AFB$_1$.

TABLE 7

AFB$_1$ cytotoxicity in CYP1A2 expressing cells

| | CD50 (AFB$_1$ ng/ml) |
|---|---|
| AHH-TK+/− | 10000 |
| AHH-1A2/Hyg | 25.0 |
| BEAS-2B-pXT1 cl4 | 4500 |
| BEAS-2B-1A2 cl8 | 50.0 |
| BEAS-2B-CMV-neo cl2 | 900 |
| BEAS-2B-CMV-1A2 cl2 | 5.5 |
| THLE-5B-CMV-neo cl5.16 | 200 |
| THLE-5B-CMV-neo cl5.3 | 0.15 |

Table 7 shows the CD50 values derived from the data in Table 6. The CD50 is the dose of carcinogen needed to obtain 50% survival. Similar conclusions can be drawn from this table to those discussed supra for Table 6.

Figure 11:
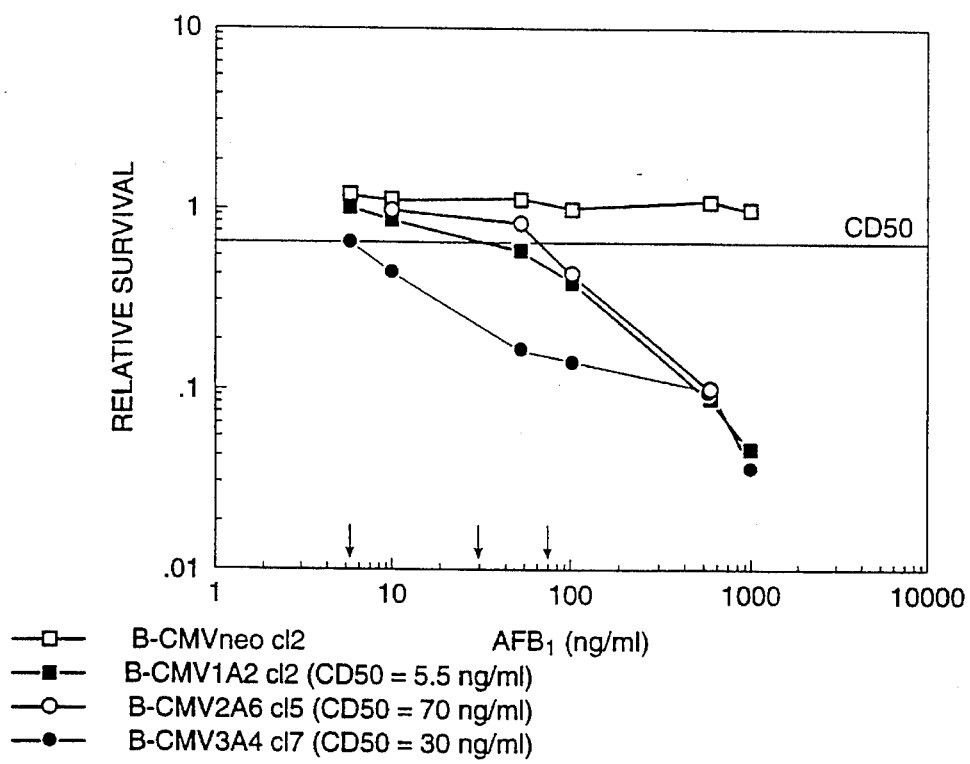
FIG. 11 shows the cytotoxicity of Aflatoxin $B_1$ in BEAS-2B-CMV-3A4, BEAS-2B-CMV-2A6, BEAS-2B-CMV-1A2 and BEAS-2B-CMV-neo cell lines.

BEAS-2B cultures containing other exogenous cytochrome P450 genes have also been tested for aflatoxin B1 cytotoxicity together with appropriate control cells. FIG. 11 shows that BEAS-2B-CMV-3A4 c17 cells (BEAS-2B cells containing an exogenous cytochrome P450 3A4 gene linked to the pCMV vector) and BEAS-2B-CMV-2A6 c15 (BEAS-2B cells containing an exogenous cytochrome P450 2A6 gene linked to the pCMV vector) exhibit greater cytotoxicity than BEAS-2B-CMV-neo c12 cells (BEAS-2B cells containing the pCMV vector but lacking an exogenous P450 gene).

B. AFB$_1$ Genotoxicity Analysis

Table 8 gives the DNA-adduct formation with AFB$_1$ for the BEAS-2B-1A2 c18 cell line compared with a BEAS-2B-pXT1 c14 control. These are the same cell lines as are described in Table 6. The formation was elevated by a factor of 1000 in clone 8.

TABLE 8

Binding of [$^3$H]AFB$_1$ to cellular DNA

| Carcinogen exposure (μg/ml) | Adduct formation (pmol/mg DNA) | |
|---|---|---|
| | BEAS-2B- pXT1 cl 4 | BEAS-2B-1A2 cl 8 |
| — | und. | und. |
| 0.1 | und. | 0.39 |
| 1.0 | 0.04 | 9.00 |

Approximately 1.10$^7$ cells were exposed to 0.1 or 1.0 μg/ml [$^3$H]AFB$_1$ (0.2 Ci/mmol) under the conditions of the cytotoxicity assay. Cellular DNA was isolated and binding was measured by liquid scintillation counting (und.: undetectable).

C. AFG$_1$ Cytotoxicity Analysis

Figure 12:
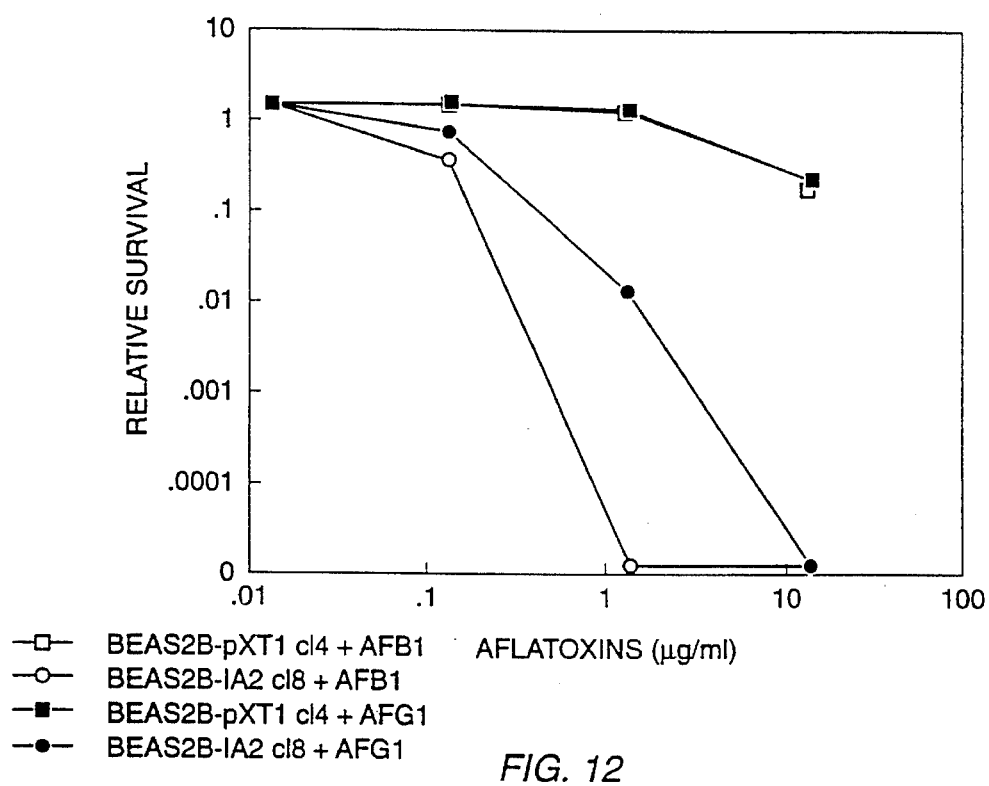
FIG. 12 shows the cytotoxicity of Aflatoxin $B_1$ or Aflatoxin $G_1$ in BEAS-2B-pXT1 and BEAS-2B-1A2 lines.

FIG. 12 shows the analysis of cytotoxicity for Aflatoxin G$_1$ in comparison with Aflatoxin B$_1$ on the BEAS-2B-pXT 1 and BEAS-2B-1A2 clones. The cells were exposed to various concentrations of the mutagens for 28 hours. Each culture contained 250 cells per 60 mm dish. After 7–10 days, cytotoxicity was determined by measuring the colony number of each plate. The colony number of the mutagen-treated cultures was divided by the colony number of the untreated cultures to yield relative survival. Each time point reflects at least 3 independent experiments. FIG. 12 shows that BEAS-2B-1A2 are more sensitive to both Aflatoxin B1 and Aflatoxin G1 than control cells lacking the exogenous cytochrome P450-1A2 gene.

D. PhIP Cytotoxicity Analysis

Figure 13:
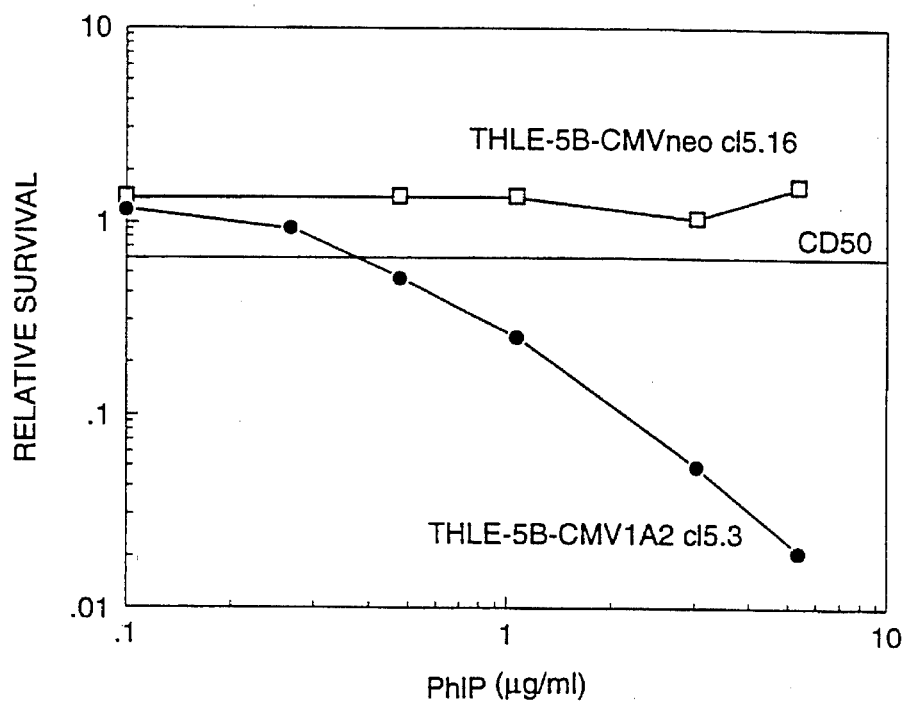
FIG. 13 shows PhIP cytotoxicity in THLE-5B-CMV-1A2 and THLE-5B-CMV-1A2 lines.

THLE-5B cells expressing cytochrome CYP1A2 from the pCMV vector were tested for PhIP cytotoxicity using the method described in Example 5.A. Cultures of cells were exposed to the indicated concentrations of PhIP. FIG. 13 shows that the THLE-5B-CMV-1A2 cl 5.3 cell line is far more sensitive to PhIP than the control strain THLE-5B-CMV-neo c15.18 (which contains the unmodified pCMV vector.)

E. Diethylnitrosame and Dimethylnitrosamine Cytotoxicity Analysis

Figure 14:
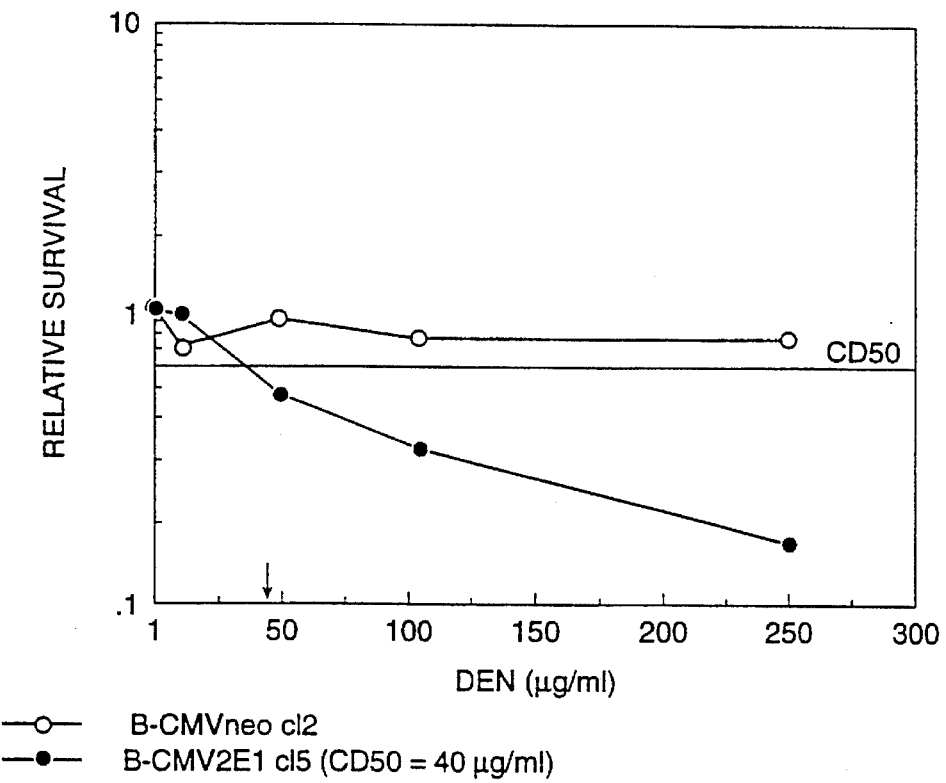
FIG. 14 shows diethylnitrosamine cytotoxicity in BEAS-2B-CMV-2E1 and BEAS-2B-CMV-neo cell lines.
Figure 15:
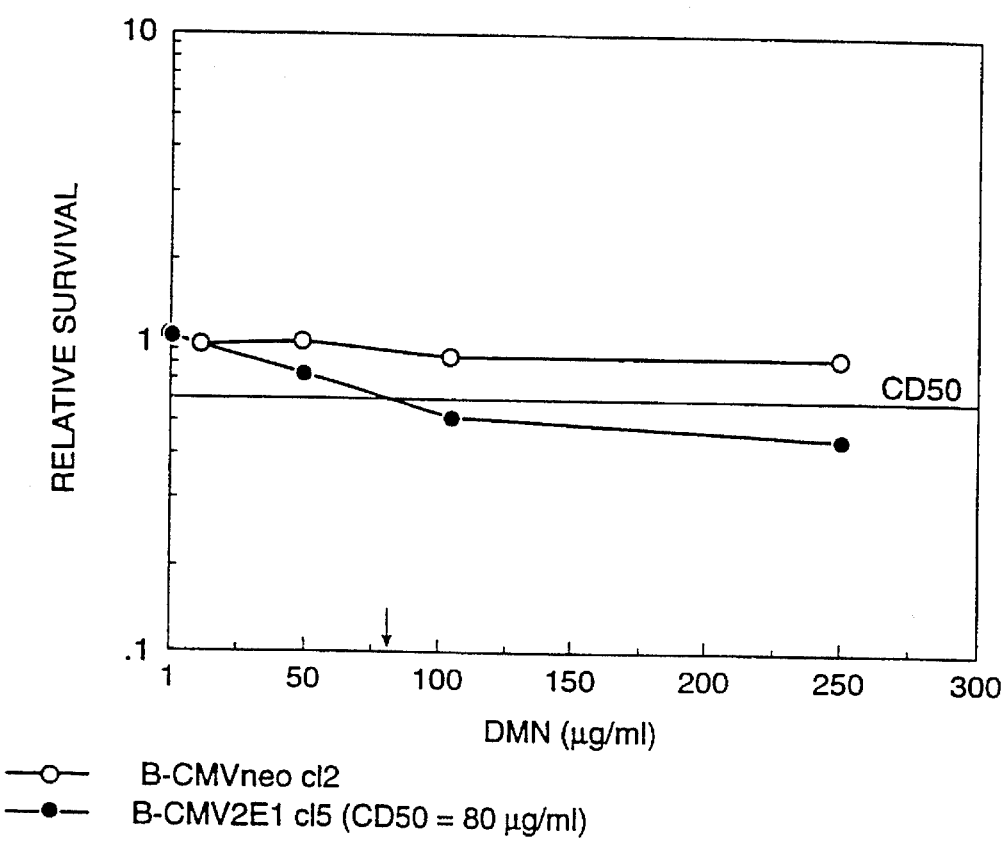
FIG. 15 shows dimethylnitrosamine cytotoxicity in BEAS-2B-CMV-2E1 and BEAS-2B-CMV-neo cell lines.

BEAS-2B cells expressing cytochrome P450 2E1 from the pCMV vector were tested for cytotoxicity to diethylnitrosamine and dimethylnitrosamine. FIGS. 14 and 15 show that these cells are more sensitive to diethylnitrosamine and dimethylnitrosamine than control cell lines containing unmodified pCMV vector.

What is claimed is:

1. A non-tumorigenic, immortalized, human bronchial epithelial cell line containing an exogenous cytochrome P450 gene, which is expressed in said cell line; the cell line produced by inserting said exogenous cytochrome P450 gene into a BEAS-2B cell line, deposited as ATCC CRL 9609, or a homolog or derivative of the BEAS-2B cell line.

2. The cell line of claim 1 wherein said exogenous cytochrome P450 gene is 1A1, 1A2, 3A4, 2C9, 2D6, and/or 2E1.

3. The cell line of claim 2, wherein said exogenous cytochrome p450 gene is operably linked to a cytomegalovirus promoter.

4. A diagnostic kit comprising the cell line of claim 1, media for propagating said cell line and reagents for diagnosing a response of said cell line to a carcinogenic, mutagenic or toxic agent.

5. A non-tumorigenic, immortalized, human adult liver epithelial cell line containing an exogenous cytochrome P450 gene which is expressed in said cell line, said cell line produced by inserting said exogenous cytochrome P450 gene into a THLE-5B cell line, deposited as ATCC CRL 11113, or a homolog or derivative of the THLE-5B cell line.

6. The cell line of claim 5, wherein said exogenous cytochrome P450 gene is 1A1, 1A2, 2A6, 3A3, 3A4, 2B6, 2B7, 2C9, 2D6, and/or 2E1.

7. The cell line of claim 6 which is selected from the group consisting of THLE-5B-1A1, THLE-5B-1A2, THLE-5B-2A6, THLE-5B-3A3, THLE-5B-3A4, THLE- 5B-2B6, THLE-5B-2B7, THLE-5B-2C9, THLE-5B-2D6, THLE-5B-2E1, and a homolog or derivative of said cell line.

8. The cell line of claim 7, wherein said exogenous cytochrome P450 gene is operably linked to a cytomegalovirus promoter.

9. The cell line of claim 6, wherein said cell line is THLE-5B-1A2, or a homolog or derivative thereof.

10. The cell line of claim 5, produced by inserting said exogenous cytochrome P450 gene into said THLE-5B cell line.

11. A diagnostic kit comprising the cell line of claim 5, media for propagating said cell line and reagents for diagnosing a response of said cell line to a carcinogenic, mutagenic or toxic agent.

* * * * *